United States Patent
Lo et al.

(10) Patent No.: US 7,815,575 B2
(45) Date of Patent: Oct. 19, 2010

(54) ULTRASONIC MONITOR WITH A BIOCOMPATIBLE OIL BASED TRANSMISSION MEDIUM

(75) Inventors: Thomas Ying-Ching Lo, Fremont, CA (US); Rong Jong Chang, Fremont, CA (US)

(73) Assignee: Salutron, Inc., Fremont, CA (US)

( * ) Notice: Subject to any disclaimer, the term of this patent is extended or adjusted under 35 U.S.C. 154(b) by 1046 days.

(21) Appl. No.: 11/124,707

(22) Filed: May 9, 2005

(65) Prior Publication Data

US 2006/0264756 A1    Nov. 23, 2006

(51) Int. Cl.
*A61B 8/14* (2006.01)
*A61B 8/00* (2006.01)

(52) U.S. Cl. ...................... 600/459; 600/437
(58) Field of Classification Search ................. 600/437, 600/443–445, 453–455, 459, 461, 500; 424/9.5, 424/427, 484; 73/644; 607/59, 88
See application file for complete search history.

(56) References Cited

U.S. PATENT DOCUMENTS

| | | | | |
|---|---|---|---|---|
| 4,364,783 A | * | 12/1982 | Theodore et al. | 156/69 |
| 4,556,066 A | * | 12/1985 | Semrow | 600/459 |
| 4,840,789 A | * | 6/1989 | Orr et al. | 424/66 |
| 4,947,859 A | * | 8/1990 | Brewer et al. | 600/528 |
| 4,982,756 A | * | 1/1991 | Scribner | 137/4 |
| 5,394,877 A | * | 3/1995 | Orr et al. | 600/459 |
| 5,494,038 A | * | 2/1996 | Wang et al. | 600/459 |
| 5,522,878 A | * | 6/1996 | Montecalvo et al. | 600/459 |
| 5,575,291 A | * | 11/1996 | Hayakawa et al. | 600/459 |
| 5,579,769 A | * | 12/1996 | Yoshida et al. | 600/437 |
| 5,628,989 A | * | 5/1997 | Harashima et al. | 424/65 |
| 5,654,362 A | * | 8/1997 | Schulz et al. | 524/862 |
| 5,727,550 A | * | 3/1998 | Montecalvo | 600/386 |
| 5,770,801 A | * | 6/1998 | Wang et al. | 73/644 |
| 5,904,654 A | * | 5/1999 | Wohltmann et al. | 600/481 |
| 5,919,437 A | * | 7/1999 | Lee et al. | 424/68 |
| 6,039,694 A | * | 3/2000 | Larson et al. | 600/459 |
| 6,132,378 A | * | 10/2000 | Marino | 600/459 |
| 6,274,120 B1 | * | 8/2001 | Dugstad et al. | 424/9.322 |
| 6,331,289 B1 | * | 12/2001 | Klaveness et al. | 424/9.52 |
| 6,359,190 B1 | | 3/2002 | Ter-Ovanesyan et al. | |
| 6,394,960 B1 | * | 5/2002 | Shinogi et al. | 600/503 |

(Continued)

OTHER PUBLICATIONS

Byk Gardner, "Digital Cone & Plate Brookfield Viscometers", Altana Chemie, http://www.bykgardner.com/html/byk.brookfield-viscometers.htm, 2004.

(Continued)

*Primary Examiner*—Long V Le
*Assistant Examiner*—Angela M Hoffa
(74) *Attorney, Agent, or Firm*—Vierra Magen Marcus & DeNiro LLP

(57) ABSTRACT

An ultrasonic monitor implemented on a PCB includes a transmission medium. The transmission medium may be biocompatible and implemented as an oil-based transmission medium, a gel pad, or a combination thereof. Ultrasonic signals are transmitted between the ultrasonic monitor and a living subject through the transmission medium. An air gap is formed in the PCB underneath transducer elements to provide for more efficient signal transmission. The entire ultrasonic monitor may be encapsulated in plastic, a transmission medium, or both to provide water resistant properties.

32 Claims, 16 Drawing Sheets

U.S. PATENT DOCUMENTS

| | | | |
|---|---|---|---|
| 6,406,684 B1* | 6/2002 | Fecht et al. | 424/65 |
| 6,447,456 B1* | 9/2002 | Tsubata | 600/455 |
| 6,478,739 B1* | 11/2002 | Hong | 600/437 |
| 6,680,047 B2* | 1/2004 | Klaveness et al. | 424/9.52 |
| 6,716,169 B2 | 4/2004 | Muramatsu et al. | |
| 6,719,699 B2* | 4/2004 | Smith | 600/459 |
| 6,744,178 B2* | 6/2004 | Muramatsu et al. | 310/334 |
| 6,783,766 B2* | 8/2004 | Pate et al. | 424/401 |
| 6,843,771 B2* | 1/2005 | Lo et al. | 600/459 |
| 6,866,630 B2* | 3/2005 | Larson et al. | 600/437 |
| 6,922,592 B2* | 7/2005 | Thompson et al. | 607/59 |
| 6,924,587 B2* | 8/2005 | Muramatsu et al. | 310/334 |
| 7,056,496 B2* | 6/2006 | Pate et al. | 424/59 |
| 7,261,876 B2* | 8/2007 | Arbogast et al. | 424/9.1 |
| 7,275,298 B2* | 10/2007 | Schindel | 29/594 |
| 7,347,989 B2* | 3/2008 | Walling et al. | 424/65 |
| 7,452,551 B1* | 11/2008 | Unger et al. | 424/452 |
| 7,547,282 B2* | 6/2009 | Lo et al. | 600/459 |
| 2001/0034486 A1* | 10/2001 | Larson et al. | 600/461 |
| 2001/0039380 A1* | 11/2001 | Larson et al. | 600/437 |
| 2002/0188198 A1* | 12/2002 | Hong | 600/437 |
| 2003/0175354 A1* | 9/2003 | Drizen et al. | 424/486 |
| 2004/0097807 A1* | 5/2004 | Smith et al. | 600/437 |
| 2004/0186384 A1* | 9/2004 | Babaev | 600/489 |
| 2004/0267234 A1* | 12/2004 | Heart et al. | 604/500 |
| 2005/0074407 A1* | 4/2005 | Smith | 424/9.5 |
| 2005/0137656 A1* | 6/2005 | Malak | 607/88 |
| 2005/0215901 A1* | 9/2005 | Anderson et al. | 600/445 |
| 2006/0127316 A1* | 6/2006 | Smith | 424/9.5 |
| 2006/0246111 A1* | 11/2006 | Smith | 424/427 |
| 2007/0172428 A1* | 7/2007 | Arbogast et al. | 424/9.52 |
| 2009/0297441 A1* | 12/2009 | Canham et al. | 424/1.61 |

OTHER PUBLICATIONS

ASTM International, "Standard Test Method for Drop Melting Point of Petroleum Wax Including Petrolatum", ASTM, 2004, D 127-87, West Conshohocken, Pennsylvania, United States.

ASTM International, "Standard Test Method for Cone Penetration of Petrolatum", ASTM, 2004, D 937-04, West Conshohocken, Pennsylvania, United States.

ASTM International, "Standard Test Methods for Rheological Properties of Non-Newtonian Materials by Rotational (Brookfield) Viscometer", ASTM, 1991, D 2196-86, West Conshohocken, Pennsylvania, United States.

* cited by examiner

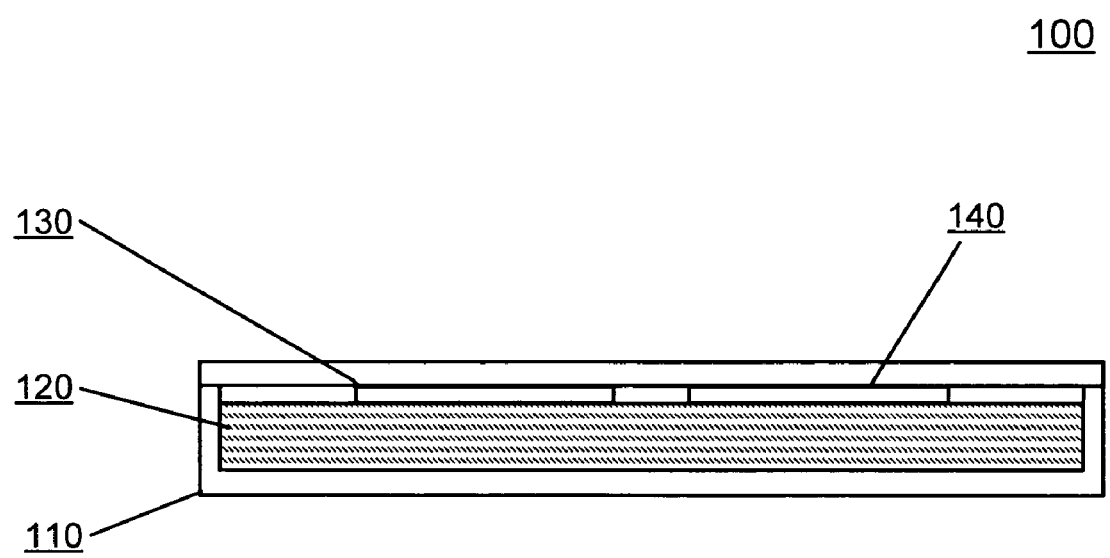
Figure 1 – Prior Art

1180

1190

ULTRASONIC MONITOR WITH A BIOCOMPATIBLE OIL BASED TRANSMISSION MEDIUM

CROSS REFERENCE TO RELATED INVENTION

The instant non-provisional application is related to the following patent applications, all of which are hereby incorporated by reference in their entirety:

U.S. Pat. No. 6,843,771, filed on Jan. 15, 2003, entitled "ULTRASONIC MONITOR FOR MEASURING HEART RATE and BLOOD FLOW RATE," having inventors Thomas Ying-Ching Lo, Tolentino Escorcio, Rong Jong Chang;

U.S. patent application Ser. No. 10/990,794, filed on Nov. 17, 2004, entitled "ULTRASONIC MONITOR FOR MEASURING BLOOD FLOW AND PULSE RATES", having inventor Thomas Ying-Ching Lo, attorney docket number SALU-01002US0; and U.S. patent application Ser. No. 10/991,115, filed on Nov. 17, 2004, entitled "GEL PAD FOR USE WITH AN ULTRASONIC MONITOR", having inventors Thomas Ying-Ching Lo, Rong Jong Chang, attorney docket number SALU-01002US0.

BACKGROUND OF THE INVENTION

1. Field of the Invention

The present invention relates to ultrasonic monitors for measuring heart rates and pulse rates in living subjects.

2. Description of the Related Art

Measuring heart and pulse rates in living subjects has become a valuable tool during physical exercise and for health monitoring. The heart rate and pulse rate of a subject are related. Heart rate may be defined as the number of heart contractions over a specific time period, usually defined in beats per minute. A pulse is defined as the rhythmical dilation of a vessel produced by the increased volume of blood forced through the vessel by the contraction of the heart. Since heart contractions normally produce a volume of blood that can be measured as a pulse, heart rate and pulse rate are ideally the same. However, a pulse rate may differ from the heart rate during irregular heart beats or premature heart beats. In this case, a heart contraction may not force enough blood through a blood vessel to be measured as a pulse.

A pulse rate is measured by counting the rate of pulsation of a subject's artery. The heart rate is measured by sensing the electrical activity of the heart based on electrocardiograms (for example EKG or ECG). Individuals who want to increase their endurance or performance may wish to exercise while maintaining target heart rates. Conversely, subjects with a history of heart disease or other heart related condition should avoid exceeding a certain heart or pulse rate to reduce unnecessary strain on their heart.

Most subjects that require continuous heart rate readings choose a monitor that requires a chest strap. Though they provide heart rates continuously, chest straps are cumbersome and generally undesirable to wear. In addition to chest strap solutions, portable patient monitors (e.g., vital signs monitors, fetal monitors) can perform measuring functions on subjects such as arrhythmia analysis, drug dose calculation, ECG waveforms cascades, and others. However, such monitors are usually fairly large and are attached to the subject through uncomfortable wires.

Pulse rate can be measured at the wrist. The shallow depth of the radial artery in the wrist offers a number of advantages for achieving continuous pulse detection at the wrist. Prior sensors that monitor pressure pulses in the wrist have not been effective. Pressure pulses are attenuated by the tissues between the artery and the sensor. Most of the high frequency signal components are lost because of the attenuation. Additionally, muscle movement may create substantial noise at the pressure sensors. The low frequency noise signals make it very difficult to reliably identify low frequency blood pressure pulses.

Ultrasonic monitors using sonar technology were developed to overcome noise signal problems. Ultrasonic monitors transmit ultrasonic energy as a pulse signal. When a power source drives a transducer element, such as a piezoelectric crystal, to generate the pulse signal, the ultrasonic pulse signal is generated in all directions, including the direction of the object to be measured such as a blood vessel. The portion of the ultrasonic pulse signal reaching the vessel is then reflected by the vessel. When the blood vessel experiences movement, such as an expansion due to blood flow from a heart contraction, the reflected pulse signal experiences a frequency shift, also known as the Doppler shift.

When either the source of an ultrasonic signal or the observer of the sonar signal is in motion, an apparent shift in frequency will result. This is known as the Doppler effect. If R is the distance from the ultrasonic monitor to the blood vessel, the total number of wavelengths $\lambda$ contained in the two-way path between the ultrasonic monitor and the target is $2R/\lambda$. The distance R and the wavelength $\lambda$ are assumed to be measured in the same units. Since one wavelength corresponds to an angular excursion of $2\pi$ radians, the total angular excursion $\phi$ made by the ultrasound wave during its transit to and from the blood vessel is $4\pi R/\lambda$ radians. When the blood vessel experiences movement, R and the phase $\phi$ are continually changing. A change in $\phi$ with respect to time is equal to a frequency. This is the Doppler angular frequency $W_d$, given by $$W_d = 2\pi f_d = \frac{d\Phi}{dt} = \frac{4\pi}{\lambda}\frac{dR}{dt} = \frac{4\pi V_r}{\lambda}$$

where $f_d$ is the Doppler frequency shift and $V_r$ is the relative (or radial) velocity of target with respect to the ultrasonic monitor.

The amount of the frequency shift is thus related to the speed of the moving object from which the signal reflects. Thus, for heart rate monitor applications, the flow rate or flow velocity of blood through a blood vessel is related to the amount of Doppler shift in the reflected signal.

A piezoelectric crystal may be used both as the power generator and the signal detector. In this case, the ultrasonic energy is emitted in a pulsed mode. The reflected signal is then received by the same crystal after the output power source is turned off. The time required to receive the reflected signal depends upon the distance between the source and the object. Using a single crystal to measure heart rates requires high speed power switching due to the short distance between source and object. In addition, muscle movement generates reflections that compromise the signal-to-noise-ratio in the system. The muscle movement noise has a frequency range similar to the frequency shift detected from blood vessel wall motion. Therefore, it is very difficult to determine heart rates with this method. The advantage of this approach, however, is low cost and low power consumption.

In some ultrasonic signal systems, two piezoelectric elements are used to continuously measure a pulse. The two elements can be positioned on a base plate at an angle to the direction of the blood. In continuous pulse rate measurement, the Doppler shift due to blood flow has a higher frequency than the shifts due to muscle artifacts or tissue movement. Therefore, even if the muscle motion induced signals have larger amplitudes, they can be removed by a high pass filter to retain the higher frequency blood flow signals. The disadvantages of continuous mode over pulsed mode are higher cost and more power consumption Several wrist mounted ultrasonic monitor devices are known in the art. However, ultrasonic signals are prone to diffraction and attenuation at the interface of two media of different densities. Thus, air in the media or between the monitor and the subject's skin make ultrasonic energy transmission unreliable. Prior ultrasonic monitors require applying water or an aqueous gel between the transducer module and the living subject to eliminate any air gap. Because water and aqueous gels both evaporate quickly in open air, they are not practical solutions.

U.S. Pat. No. 6,843,771 disclosed the use of thermoplastic and thermoset gels as the transmission medium for ultrasonic signals to overcome the problems associated with water and aqueous gel solutions. In U.S. Pat. No. 6,716,169, Muramatsu et al. disclosed a soft contact layer based on silicone gel, a type of thermoset gel, as the medium for the ultrasonic signal transmission. These gels mainly consist of a large quantity of non-evaporating (at ambient condition) liquid diluents entrapped in a lightly cross-linked elastomeric network. These cross-linked networks can be either physical in nature, such as in the thermoplastic gels, or chemical in nature, such as the thermoset gels.

Synthetic thermoset and thermoplastic gels have disadvantages. The liquid diluents, though entrapped in the elastomeric network, can still diffuse into the skin of a user upon contact over a period of time. Since silicone gels use silicone oil as diluents, diffusion of silicone oil is an important health concern, Diffusion of these oils into body tissues can cause biological problems. Synthetic thermoset and thermoplastic gels also tend to be soft gels. Though a softer gel allows better contact with the skin and results in better ultrasonic transmission, soft gels are weak, difficult to handle and difficult to attach to ultrasonic transmitters.

Efficiency of the transmitting transducer is an important feature in wrist worn and other small heart rate monitors. Transmission of an ultrasonic signal by a transmitting transducer can be made more efficient by use of a reflector. Transmission signals generated away from target can be reflected using a reflector on one or more sides of the transducer. Some heart rate monitors include a foam substance having air voids underneath the piezoelectric crystals. As illustrated in FIG. 1, a foam layer 120 may be placed within ultrasonic module 110 underneath transducers 130 and 140. The foam material air voids partially inhibit ultrasound energy penetration and provide fairly effective reflection of ultrasound signals. With this foam backing, some of the ultrasonic signals directed towards the foam are reflected toward the desired direction. The disadvantage to incorporating foam layers is that they are manually installed during manufacture. Other prior systems increase efficiency by separating the two piezoelectric crystals by a channel on a base plate. This reduces crosstalk between the transducers to some degree but does not eliminate the loading or dampening effect caused by the base plate.

Heart rate monitors that provide continuous heart rate readings through a transmission media are useful. The transmission media should be biocompatible and not dry out during the monitoring, leave an uncomfortable wet film, or be difficult to generate and apply.

SUMMARY OF THE INVENTION

The present invention, roughly described, pertains to ultrasonic monitors. The ultrasonic monitor uses ultrasonic signals to measure movement inside the body of a living subject. The movement may be a heart contraction, flowing blood or movement of the blood vessel itself. From information collected from these movements, electronics within the monitor may determine blood flow rate, heart rate, or pulse rate of the living subject.

In some embodiments, a biocompatible oil-based transmission medium is used to transmit ultrasonic signals between an ultrasonic monitor module and a subject. The biocompatible oil-based transmission medium is positioned in contact with the ultrasonic monitor module and the subject, and provides transmission of ultrasonic signals between the ultrasonic monitor module and the subject.

In some embodiments, an ultrasonic monitor may include a transmission transducer, a receiving transducer, a housing and biocompatible oil-based transmission medium. The transmission transducer can be configured to transmit an ultrasonic signal and the receiving transducer can be configured to receive a reflected ultrasonic signal. The housing may contain the transmission transducer and the receiving transducer. The biocompatible oil-based transmission medium is in contact with the housing. The ultrasonic signal and reflected ultrasonic signal are transmitted through the biocompatible oil-based transmission medium between the transducers and a subject.

A heart rate may be monitored by applying a biocompatible oil-based transmission medium between an ultrasonic monitor module and a subject. The ultrasonic monitor module transmits an ultrasonic signal through the biocompatible oil-based transmission medium to the subject. A reflected ultrasonic signal is received by the ultrasonic monitor module through the biocompatible oil-based transmission medium from the subject. The received ultrasonic signal is then processed.

In some embodiments, a monitor system may include an ultrasonic monitor and an oil-based transmission medium. The ultrasonic monitor may be positioned in proximity to a subject's blood vessel. The oil-based transmission medium may be positioned between the ultrasonic monitor and the subject's blood vessel. The oil-based transmission medium may comprise a wax component and an oil component and be able to transmit ultrasonic signals between the ultrasonic monitor and the subject when positioned between the ultrasonic monitor and the subject.

In some embodiments, an ultrasonic monitor may include an ultrasonic monitor module, a gel pad, and a biocompatible oil based transmission medium. The gel pad may be in contact with the ultrasonic monitor module. The biocompatible oil based transmission medium may be in contact with the gel pad and a subject. The gel pad and biocompatible oil based transmission medium may provide transmission of ultrasonic signals between the ultrasonic monitor module and the subject.

BRIEF DESCRIPTION OF THE DRAWINGS

FIG. 1 illustrates a cross section of an ultrasonic monitor of the prior art.

DETAILED DESCRIPTION

Figure 2A:
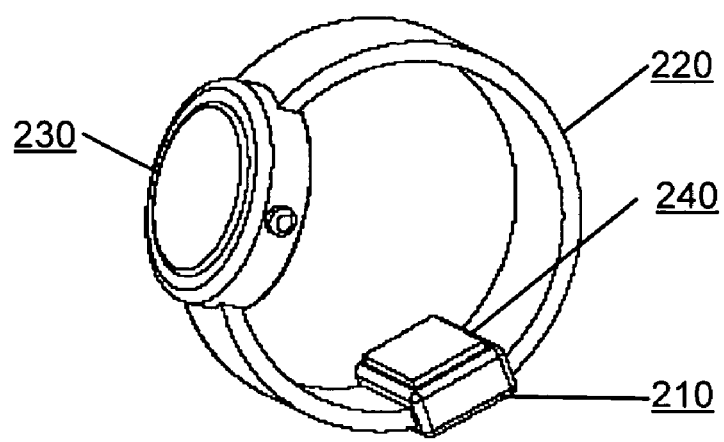
FIG. 2A illustrates one embodiment of an ultrasonic monitor with a physical connection to a display device.

The present invention, roughly described, pertains to ultrasonic monitors. The ultrasonic monitor uses ultrasonic signals to measure movement inside the body of a living subject. The movement may be a heart contraction, flowing blood or movement of the blood vessel itself. From information collected from these movements, electronics within the monitor may determine blood flow rate, heart rate, or pulse rate of the living subject.

In one embodiment, the ultrasonic monitor measures blood flow through an artery of a person. The ultrasound signals reflected by blood vessel expansion (expansion due to blood moving through the vessel) have a frequency range similar to that of noise caused by muscle artifacts and tissue movement. The ultrasound signals reflected by the flowing blood itself have a frequency range higher than muscle and tissue related noise. As a result, the signals reflected by flowing blood are easier to process to find the rate values than those reflected by expansion of the blood vessel itself.

The terms ultrasonic and ultrasound are used interchangeably herein and refer to a sound wave having a frequency between about 30 KHz and about 30 MHz. An ultrasonic transducer, or transducer element, as used herein is a device used to introduce sonic energy into and detect reflected signals from a living subject. Ultrasonic transducers respond to electric pulses from a driving device and ultrasonic pulses reflected by a subject.

The ultrasonic monitor is comprised of an electronics portion and a transmission portion. The electronics portion includes the electrical components required to transmit, receive, and process the ultrasonic signals as discussed with respect to FIGS. 3-5. Processing may include amplifying, filtering, demodulating, digitizing, squaring, and other functions typically signal processing functions. Processing may be performed all or in part by digital circuitry. For example, the received ultrasonic signal can be digitized. The processing described herein to the received signal can then be performed by digital circuitry. The transmission portion, or transmission medium, may include a biocompatible oil-based transmission medium, gel pad, or combination of the two between the monitor and the subject. In some embodiments, the oil-based transmission medium can be positioned in direct contact with the living subject and the ultrasonic monitor. In some embodiments, the oil based transmission medium is in contact with the gel pad, and the oil based transmission medium and gel pad provide transmission of ultrasonic signals between an ultrasonic monitor and a subject. Both oil based transmission mediums and gel pads are discussed in more detail below.

In one embodiment, an oil-based transmission medium used to transmit ultrasonic signals between the ultrasonic monitor and the subject may be biocompatible. A biocompatible transmission medium is one that can be in contact with a user's skin without being toxic, being injurious, causing immunological rejection or otherwise resulting in undesirable health effects, such as those caused by typical thermoset and thermoplastic gels. In one embodiment, a biocompatible oil-based transmission medium can include an oil component and a wax component. Both the oil and wax components may be natural rather than synthetic. Additional components may be included as well, including one or more "essential oils" and water. An essential oil is a natural oil that provides a fragrance, moisturizes skin, or heals skin tissue. The ratio of wax to liquid (liquids such as natural oil, essential oil and water) may determine the consistency of the biocompatible oil-based transmission medium. The biocompatible oil-based transmission medium may be applied between an ultrasonic monitor and a user's skin with an applicator device, as a disposable transmission medium component, or as part of the ultrasonic monitor. Oil-based transmission media are discussed in more detail below.

In one embodiment, the monitor of the present invention is implemented on a printed circuit board (PCB). By implementing the circuitry on a PCB, the monitor system has a very small footprint with a much lower power requirement. The transducers are mounted directly to the PCB.

The PCB can implement an ultrasound signal reflection layer. In one embodiment, a portion of the outer layer of the PCB is removed to create an air gap portion. Transducer elements are placed over the air gap portion. When driven, the transmitting crystal generates an ultrasound signal that travels towards the PCB in addition to the desired direction towards a target. The portion of the originally transmitted ultrasound signal traveling towards the PCB is reflected by the thin air gap away from the PCB and towards the intended target.

In another embodiment, the PCB can be entirely encapsulated in plastic, an adhesive, an encapsulant, a gel, or a combination of these. This provides for keeping the system of the ultrasonic monitor protected from debris such as dirt, dust and water. These advantages are discussed in more detail below.

The ultrasonic monitor may be implemented with a display. FIG. 2A illustrates a wrist worn ultrasonic monitor system 200 in one embodiment. System 200 includes an ultrasonic monitor module 210, a strap 220, a display device 230 and a transmission medium 240. Ultrasonic monitor module 210 detects blood flow through the radial artery at the subject's wrist. Heart rate data is then provided directly to display module 230. In one embodiment, connecting wires are molded into strap 220 between the ultrasonic monitor module 210 and display device 230.

Figure 2B:
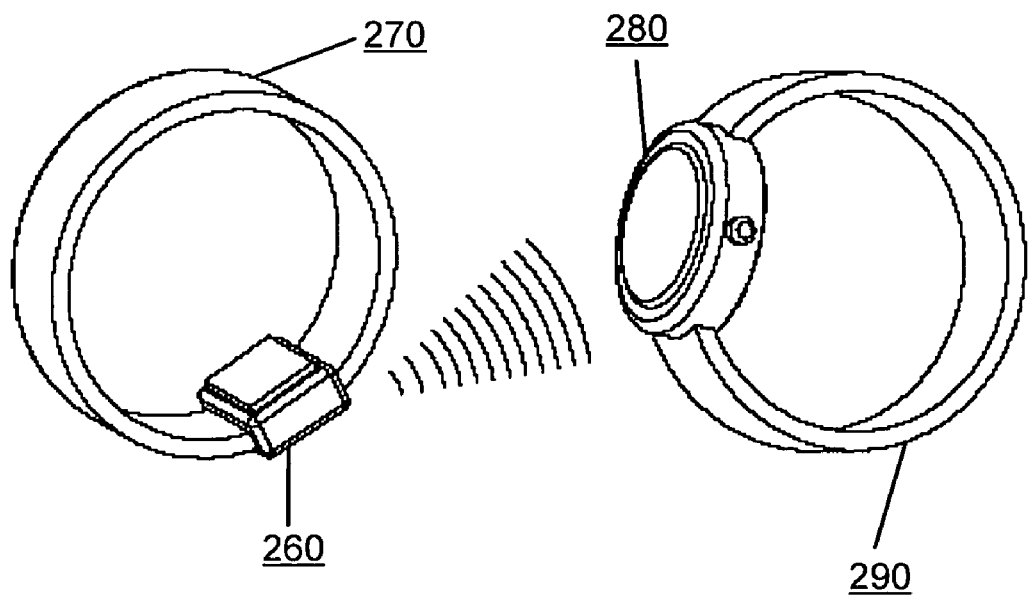
FIG. 2B illustrates one embodiment of an ultrasonic monitor with a wireless connection to a display device.

The ultrasonic monitor can also be implemented with a remote display. The ultrasonic monitor system 250 of FIG. 2B includes monitor module 260, first strap 270 attached to monitor module 260, remote display module 280 and second strap 290 attached to remote display module 280. Ultrasonic monitor module 260 detects the blood flow through the radial artery in the wrist. Heart rate data is then provided to remote display module 280. Monitor 260 can wirelessly transmit information to a remote display 280 using a wireless transmitter. The remote display 260 includes a receiver to receive the transmission from monitor 260. The remote display 280 may also be a monitor screen or other device. The ultrasonic monitor module 280 may be attached to another part of the body (such as the chest over the subject's heart) with a biocompatible adhesive or a transmission medium.

Determining what ultrasound signal frequency to use may depend on the particular object being monitored. The wrist offers a convenient location for positioning the monitoring device. The relatively shallow focal depth of the radial artery in the wrist suggests using a high frequency carrier signal.

The size of the transducer elements also affects the ultrasound signal frequency. Thinner electromechanical resonators emit at higher frequencies. Transducer elements driven by high frequency signals tend to vibrate more rapidly and consume more power than those operating at lower frequencies. This is primarily due to internal loss. The ultrasonic monitor amplifier and demodulation circuits will also consume more power processing the higher frequencies.

Figure 3:
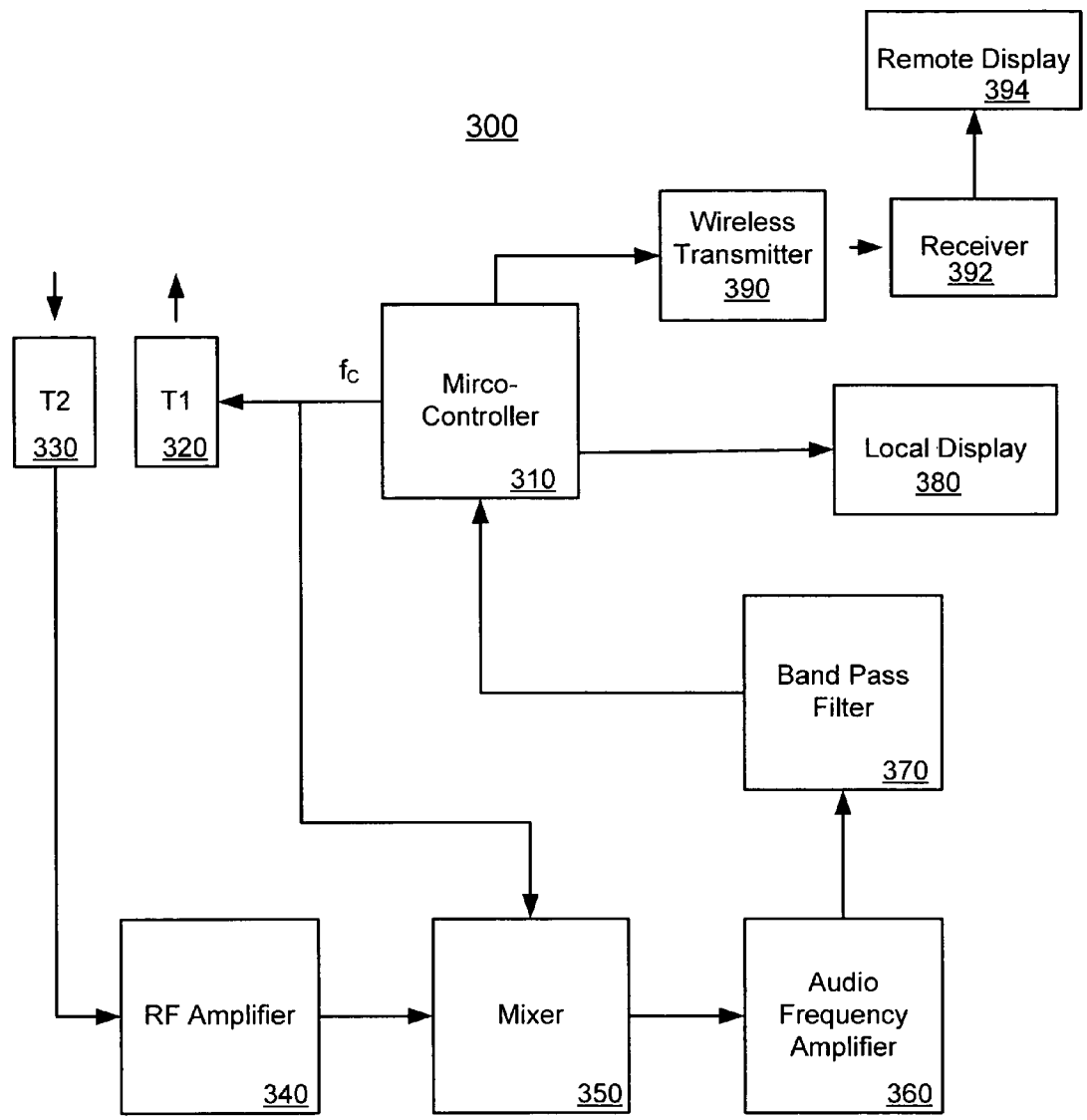
FIG. 3 illustrates one embodiment of a block diagram of an ultrasonic monitor.

A block diagram of one embodiment of an ultrasonic monitor system 300 is illustrated in FIG. 3. Ultrasonic monitor system 300 includes a microcontroller 310, a transmitting transducer element 320 connected to microcontroller 310, a receiving transducer element 330, a radio frequency (RF) amplifier 340 connected to receiving transducer 330, a mixer 350 connected to RF amplifier 340 and microcontroller 310, an audio amplifier 360 connected to mixer 350, and band pass (BP) filter 370 connected to audio frequency amplifier 360 and microcontroller 310. Ultrasonic monitor system 300 may optionally include a local display 380 connected to microcontroller 310, a wireless transmitter 390 connected to microcontroller 310, a wireless receiver 392 receiving a wireless signal from wireless transmitter 390, and a remote display 394 connected to receiver 392.

In one embodiment, an ultrasonic monitor can be implemented with a system similar to that represented by block diagram 300, but with a driver circuit and high pass and low pass filters. In this case, the microcontroller drives driver circuitry with a carrier signal. The driver circuitry drives transmitting transducer to transmit an ultrasonic signal at a carrier frequency. The ultrasonic signal is reflected and received by receiving transducer. The received signal includes a frequency shift from the signal transmitted by transducer. The received ultrasonic signal is amplified by RF amplifier circuitry. The amplified ultrasonic signal is then processed by a mixer, which demodulates the received signal and generates a signal with an audio range frequency. The resulting signal is then amplified by an audio frequency amplifier circuit. The amplified audio signal is then filtered by a high pass filter circuit and a low pass filter circuit. The filtered signal is then received by the microcontroller. The microcontroller processes the filtered signal and provides an output signal to a wireless transmitter. The wireless transmitter transmits the signal through a wireless means to a receiver. A display then receives the signal from the receiver and displays information derived from the signal.

Figure 4:
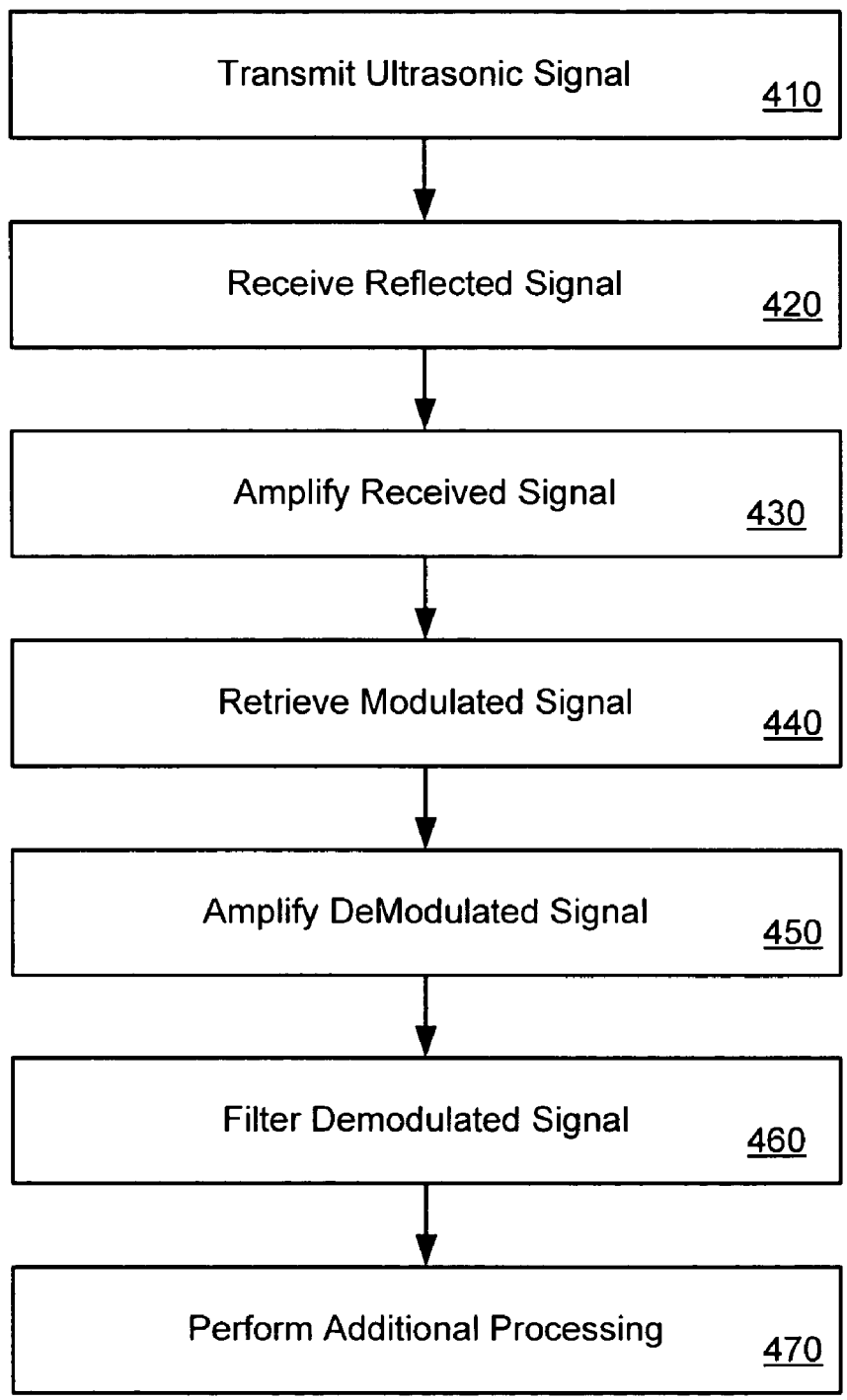
FIG. 4 illustrates one embodiment of a method of operation of an ultrasonic monitor.
Figure 5:
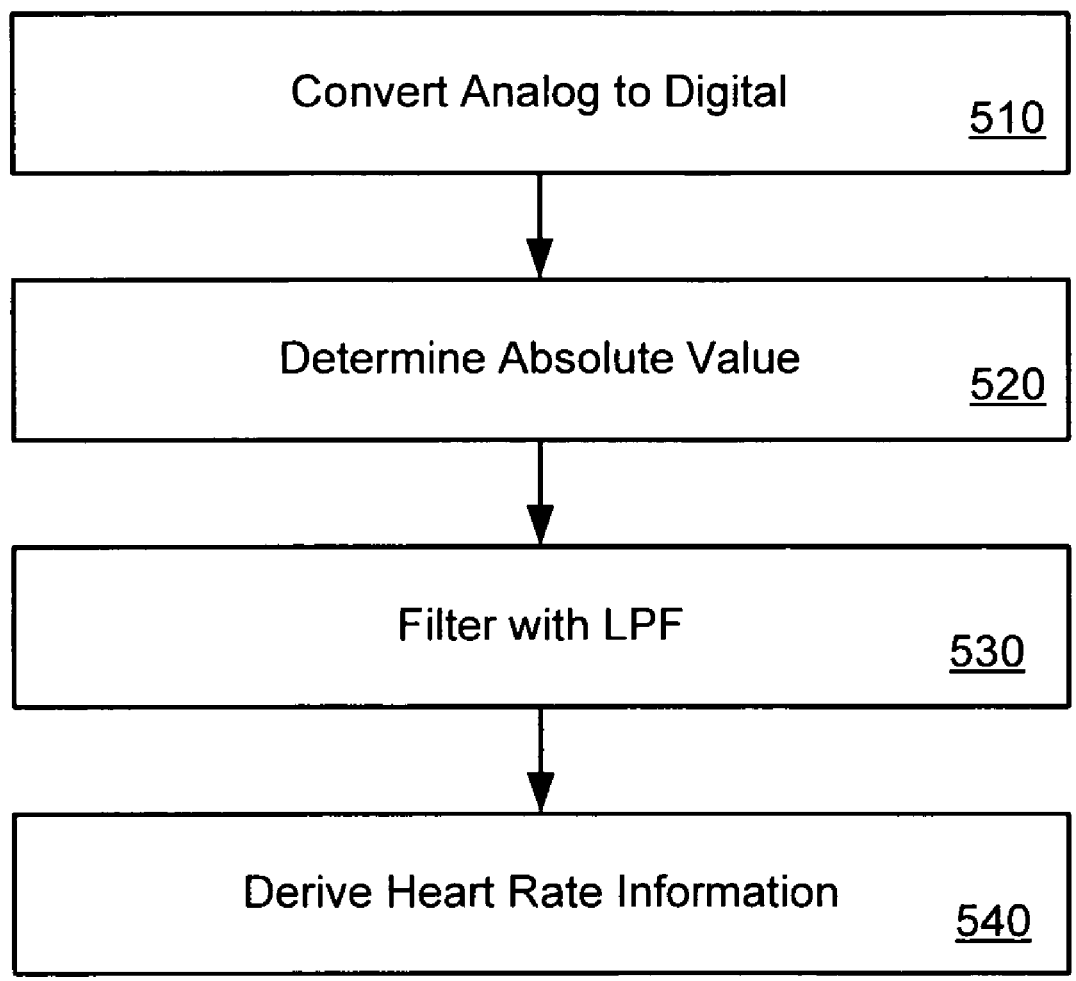
FIG. 5 illustrates one embodiment of a method for performing additional processing by an ultrasonic monitor.

Method 400 of FIG. 4 illustrates the operation of one embodiment of an ultrasonic monitor such as that represented in FIG. 3. An ultrasound signal is transmitted at step 410. With respect to system 300, microcontroller 310 drives a transmitting transducer element 320 with a carrier signal $f_C$. As a result, the transmitting transducer generates an ultrasound signal. In one embodiment, the carrier signal may be within a range of 30 KHz to 30 MHz. In another embodiment, the carrier signal may be within a range of 1 MHz to 10 MHz. In yet another embodiment, the carrier signal is about 5 MHz.

A reflected ultrasonic signal is received at step 420. The reflected ultrasonic signal is generated by the reflection of the ultrasonic signal of step 410 from a blood vessel. When the ultrasonic monitor is worn on a wrist, the radial artery reflects the signal. The received ultrasonic signal will contain an ultrasonic carrier frequency that has experienced a Doppler shift from the signal transmitted by transmitting transducer 320. The received signal is then amplified at step 430. In one embodiment, the amplifier 340 of system 300 is implemented as a radio frequency amplifier. The received ultrasonic signal is amplified by a factor that allows it to be processed for demodulation. Once the ultrasonic signal is amplified at step 430, it is processed by mixer 350 at step 440. The mixer uses the carrier signal $f_C$ to demodulate the reflected ultrasonic signal in order to extract the Doppler signal. Accordingly, mixer 350 is driven by carrier signal $f_C$. and the reflected ultrasound signal. The output signal provided by mixer 350 is then amplified at step 450 by amplifier 360. As the output of the mixer will have a frequency component in the audio range, Amplifier 360 is an audio amplifier designed to amplify the demodulated audio range Doppler frequencies.

After the demodulated signal has been amplified, the amplified signal is filtered at step 460. In one embodiment, the filter of step 460 is a band pass filter. The band pass filter may be configured to remove aliasing effects, noise, and other unwanted frequency elements. In another embodiment, the band pass filter may be implemented with a high pass and low pass filter. After the signal is filtered at step 460, the signal is subject to additional processing at step 470.

The additional processing of step 470 may include several steps depending on the ultrasonic monitor system. The processing may be performed by a microcontroller or other circuitry. Though methods vary, a typical example of additional processing is illustrated in method 500 of FIG. 5. The filtered signal from step 460 of method 400 is processed by an analog to digital converter at step 510. In one embodiment, the digitization is performed if it was not performed earlier. The absolute value of the digitized signal is then determined at step 520. Alternatively, the square of the signal may be determined at step 520. Next, the signal derived from step 520 is filtered by a low pass filter in step 530. The low pass filter removes noise and other unwanted frequency elements of the signal. The heart rate is then derived at step 540. After the processing of steps 510-530, the resulting signal is a pulse signal retrieved from the receiving transducer. The signal appears as a series of pulses, wherein each pulse has an area as determined by the path of its amplitude to and from a peak amplitude. The resulting heart rate, or pulse rate, is derived from the frequency of the pulses (for example, 160 pulses per minute corresponds to 160 heart beats per minute in step 540). The flow rate is determined by integrating the area underneath the waveform of the pulses.

The microcontroller of ultrasonic monitor can be implemented as one or more of several common microcontroller integrated circuits, including Samsung KS57C 3316 series, Samsung S3C7335, Intel 8051 series, and Texas Instruments MSP430 series microcontrollers. The mixer of the ultrasonic monitor can be implemented as one or more of several common mixer ICs or frequency modulation ICs. A non-exclusive list of possible mixer ICs include NJC's NJM2295, NJM2292 and NJM2537 mixers, Toko's TK8336IM mixer, and Motorola's MC3371 mixer.

The transducers used in the present invention adhere to some general design guidelines. The transducers of the ultrasonic monitors can be piezoelectronic transducers. The length of each transducer is generally about one centimeter long. The transducer length is also generally equal or greater than five times its width. The frequency at which a transducer operates at is generally related to the thickness of the transducer. Several types of transducers may be used in the present invention. One example is a K-350, Modified Lead Zirconate-Titanate transducer, by Keramos Division, Piezo Technologies. Equivalent materials to this type of transducer include PZT-5A or NAVY-II equivalent.

Ultrasonic Monitor on a Circuit Board

One embodiment of the ultrasonic monitor system is implemented on a printed circuit board (PCB). PCB technologies such as surface mount (SMT) and chip-on-board (COB) can be used to implement the monitor on a PCB. Implementing the circuitry on a PCB integrates the monitor system to a very small footprint. This allows for a more efficient system, lower power requirement, consistent product performance and reduced production cost.

Implementing the monitor system on a PCB allows for easy construction of an aperture, or air gap, portion. To generate the air gap portion, one or more sections of the outer layer of the PCB are removed. The transducers are then placed over the air gap portion. This creates an air gap portion having one or more air gaps underneath the transducer elements. The air gap portion reflects ultrasonic signals away from the PCB and towards the desired direction. The air gap is more effective and much more easily constructed than foam layers of prior systems. Additionally, the transducer elements are mechanically isolated as a result of the air gap, thereby reducing any dampening or loading effect on the transducers from contact by any other material. The air gap also serves to significantly reduce if not eliminate crosstalk noise between the transducers. In some embodiments, additional layers may be removed from the PCB to generate an air gap portion with a larger thickness. In this case, additional etching, drilling or other methods may be used to control the depth of the air gap. In some embodiments, an air gap may be generated that penetrates the entire circuit board. This method provides for simple generation of an air gap that effectively reflects the ultrasound signal.

The ultrasonic monitor transmits ultrasound signals more efficiently than prior monitors. The ultrasonic monitor transducers are mounted directly to the PCB using conductive epoxy or solder paste. Transducers of previous systems are typically glued entirely to a supporting structure, such as a glass base plate. Attaching the entire surface of the transducers to a supporting structure creates a mechanical load that dampens the vibration of the transducers. The dampening reduces the efficiency and draws power from the ultrasonic signal. With a minimized load, transducers of the present invention can generate the same ultrasound signals of previous systems using less power.

The PCB may include several layers, for example, a power layer, a ground layer and an insulating layer. The insulating layer can isolate the transducers from the monitor system circuitry. In some four layer PCBs, there are four copper layers and three insulating layers. Two copper layers are outer layers and two are inner layers. In one embodiment, to isolate the two transducers electrically so that they won't interfere with the rest of the circuitry on the PCB, one of the inner copper layers immediate next to the transducers can be used as a ground plane or ground layer. This inner copper layer ground plane will shield RF interferences generated or received by the transducers. This prevents the circuitry from causing interference with the transducer signal transmissions. In one embodiment, one surface of the PCB may be used to implement the monitor system circuitry and the opposite surface may be used to mount the transducers. In another embodiment, the transducers may not be implemented on the same PCB as the monitor system circuitry.

Figure 6:
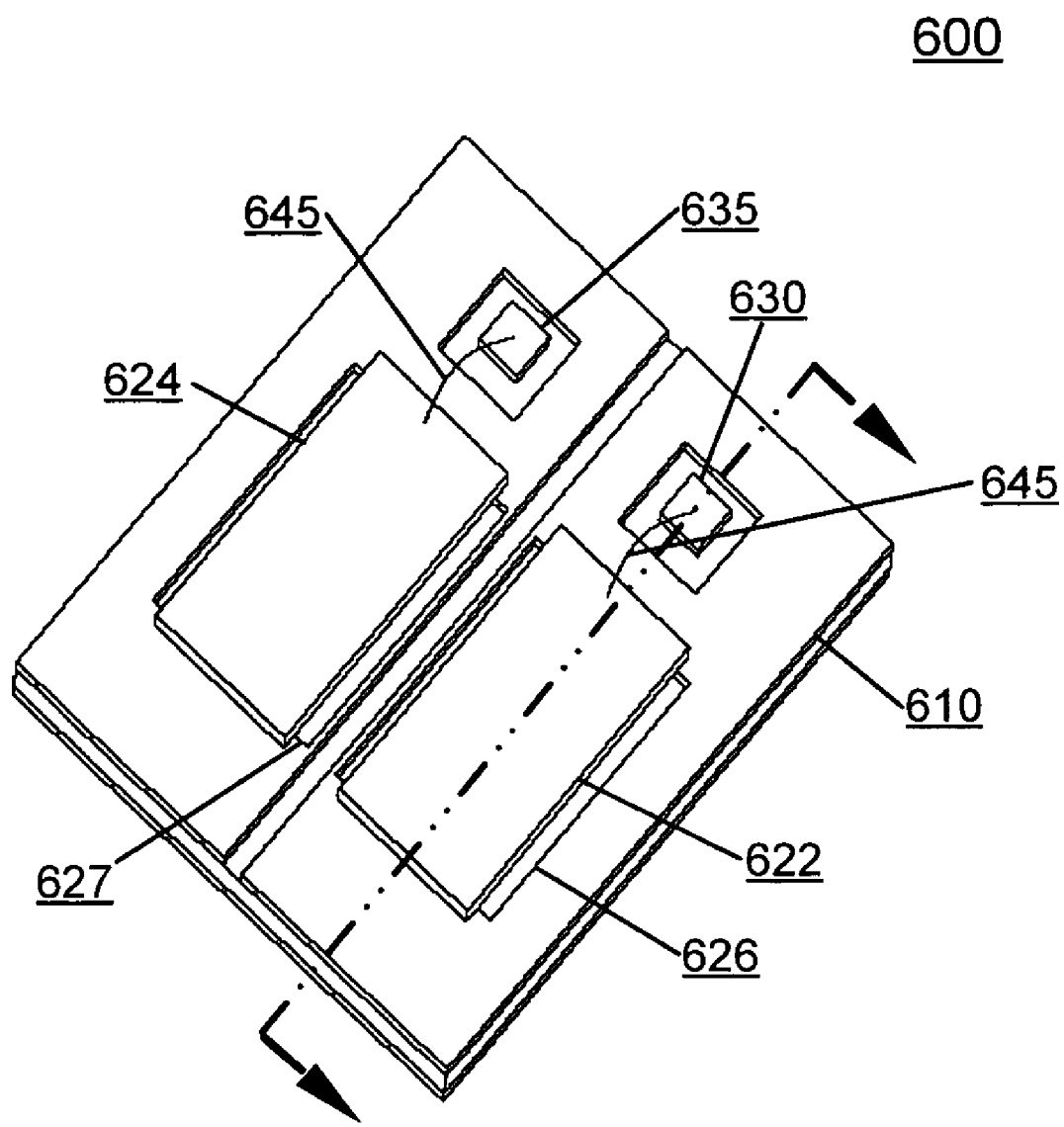
FIG. 6 illustrates one embodiment of a perspective view of an ultrasonic monitor on a PCB having an air gap.

FIG. 6 illustrates a top view of one embodiment of a monitor 600 implemented on a PCB. Monitor 600 includes outer layer 610, a first transducer 622 and a second transducer 624 mounted to outer layer 610, air gaps 626 and 627 residing underneath the transducers 622 and 624, respectively, dedicated copper pads 630 and 635, and connecting wires 640 and 645 connected between the dedicated copper pads 630 and 635 and the transducer elements 622 and 624, respectively. In one embodiment, the outer layer 610 is composed of a conducting material such as copper plated in tin or gold.

Figure 7:
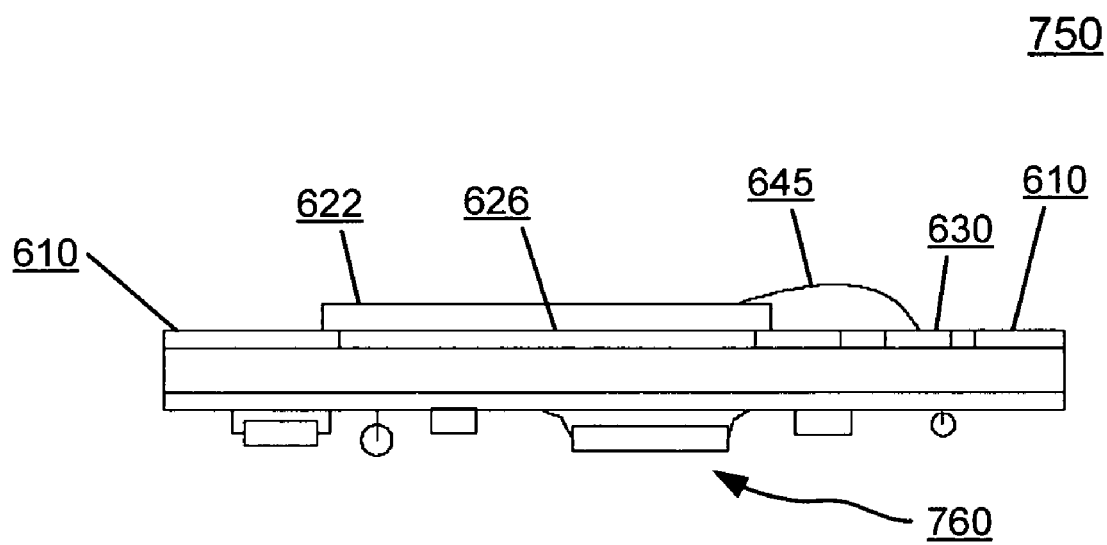
FIG. 7 illustrates one embodiment of a side view of an ultrasonic monitor on a PCB having an air gap.

FIG. 7 illustrates a side view of the monitor 750 implemented on a PCB and further illustrates circuitry 760 attached to the opposite surface of the PCB. Circuitry 760 includes surface mount ICs and electrical components such as resistors and capacitors that can implement the electrical system of the ultrasonic monitor.

Most, if not all, of the construction of the PCB can be automated. Application of solder paste, placement of the transducer elements and wire bonding can all be automated by existing PCBA production technologies. This reduces manufacturing cost significantly. For typical electronic components such as resistors, capacitors, and integrated circuits in surface mount packages, a stencil is used to apply solder paste to the PCB on one side first. An automatic pick and place machine then places these components. The PCB is then subjected to an infrared (IR) furnace which melts solder paste and forms electrical connections between the components and the underlying circuit pre-etched on the PCB. The same steps can be applied to mount the transducer elements on the opposite side of the PCB. This tremendously reduces the production cost and enhances product performance consistency.

Air gap portions 626 and 627 of FIGS. 6 and 7 are constructed by removing a portion of the outer layer. Chemical etching can be performed to remove a portion of the outer layer of a PCB. Accordingly, the depth of the air gap portion is the thickness of the layer removed. The area of outer layer 610 etched away is proportional to the surface area of the transducers 622 and 624. Air gap portions 626 and 627 are constructed so that the transducer elements 622 and 624 slightly overlap the air gap portion. This overlap of the transducer allows the ends of the transducers to be mounted to the outer layer of the PCB.

Figure 8A:
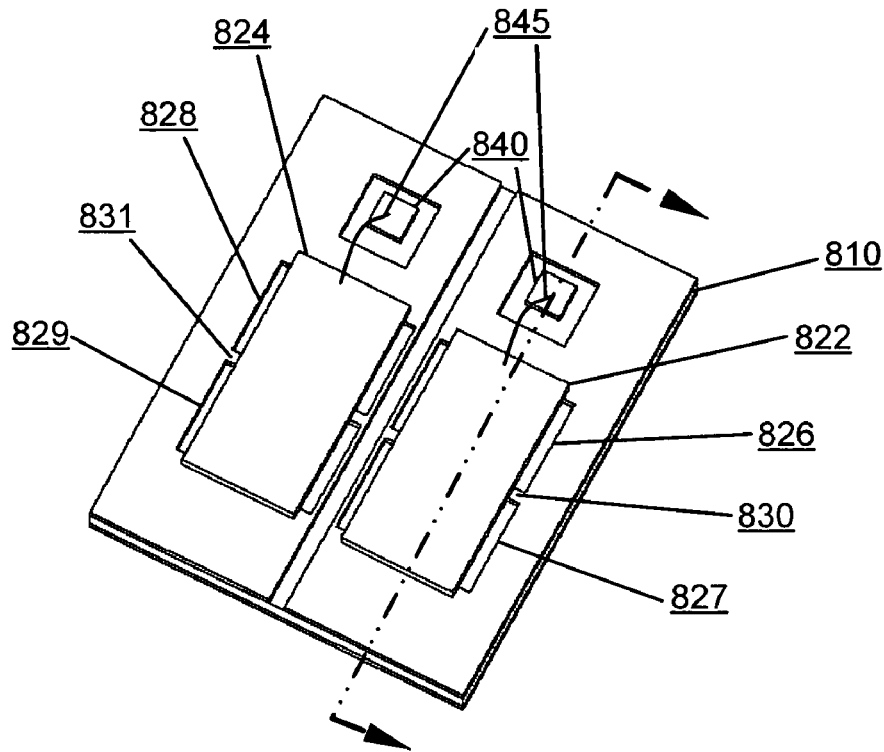
FIG. 8A illustrates one embodiment of a perspective view of an ultrasonic monitor on a PCB having an air gap with a supporting member.
Figure 8B:
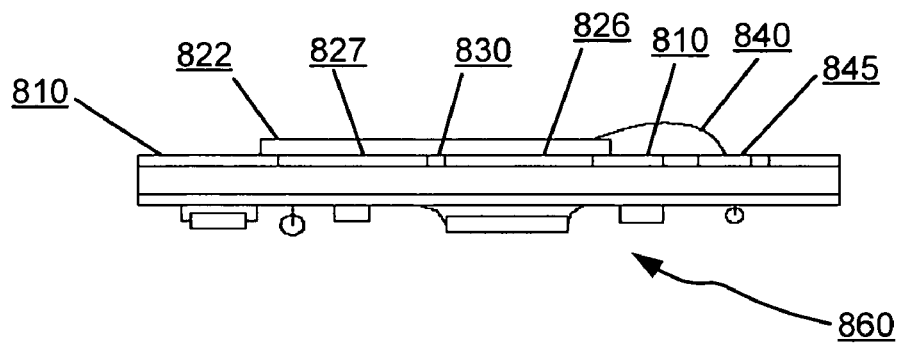
FIG. 8B illustrates one embodiment of a side view of an ultrasonic monitor on a PCB having an air gap with a supporting member.

The air gap portion of the present invention may be implemented in several ways. In the embodiment illustrated in FIGS. 6 and 7, the air gap portion is a single undivided area underneath each transducer. The air gap extends about as long as the width of the transducer and slightly shorter than the length of the transducer. FIG. 8A is a top view of an embodiment of a monitor 800 implemented on a PCB. Monitor 800 includes PCB outer layer 810, transducers 822 and 824 connected to the outer layer, air gaps 826 and 827 underneath transducer 822 and separated by supporting member 830, air gaps 828 and 829 underneath transducer 824 and separated by supporting member 831, copper contact pads 840, and connecting wires 845 connecting copper pads 840 to transducers 822 and 824. FIG. 8B is a side view of monitor 800 implemented on a PCB and further illustrates circuitry 860 attached to the opposite surface of the PCB. The air gap portion of FIGS. 8A and 8B includes two air gaps. The air gap portion extends about as long as the width of the transducer and slightly shorter than the length of the transducer. However, the air gap portion for each transducer includes a support member. Thus, the air gap portion for transducer 822 is comprised of air gap 826, air gap 827 and support member 830 and the air gap portion for transducer 824 is comprised of air gap 828, air gap 829 and support member 831.

The support member is constructed by leaving a portion of the outer layer of the PCB over which the transducer will reside. In the embodiment of FIGS. 8A and 8B, support members 830 and 831 are thin strips extending across the width of the air gap portion and located at about the middle of the length of the transducer. In different embodiments, the support members can be implemented with different shapes and locations within the air gap portion of the PCB. For example, the support member can be implemented as a strip extending less than the entire width of the air gap portion, a strip along the length of the air gap portion, or as a plurality of small regions within the air gap portion. When implemented as one or more regions, the supporting member can be isolated from the remainder of the outer layer or contact with a portion of the outer layer. The support member can support a transducer should the transducers receive pressure from an outside force.

Figure 9A:
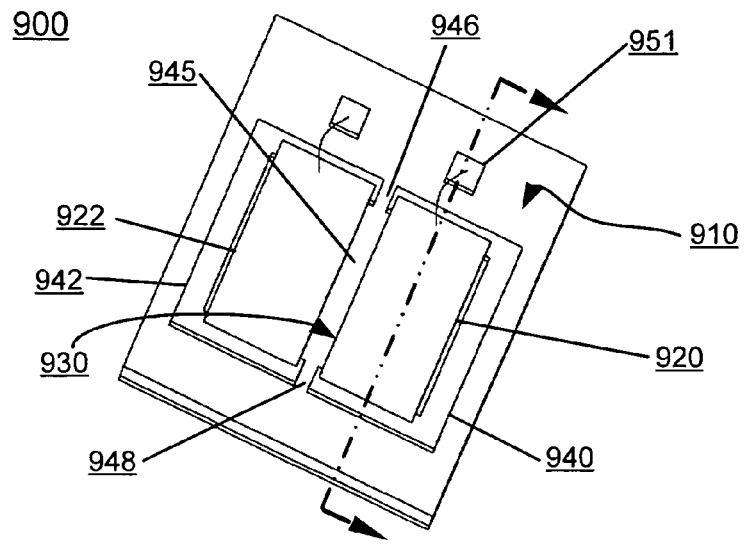
FIG. 9A illustrates one embodiment of a perspective view of an ultrasonic monitor on a PCB having one air gap shared by two transducers.
Figure 9B:
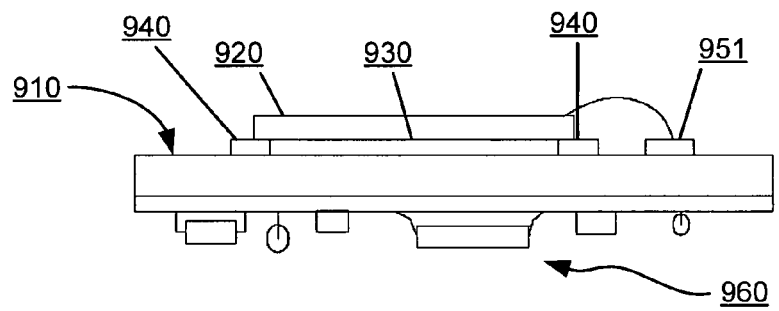
FIG. 9B illustrates one embodiment of a side view of an ultrasonic monitor on a PCB having one air gap shared by two transducers.
Figure 9C:
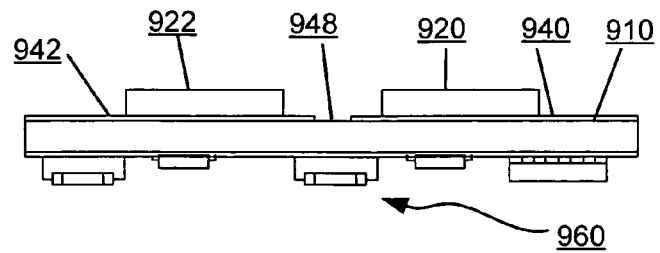
FIG. 9C illustrates one embodiment of a front view of an ultrasonic monitor on a PCB having one air gap shared by two transducers.

FIGS. 9A-C depict an embodiment of a monitor 900 implemented on a PCB. FIG. 9A provides a top view of monitor 900. Monitor 900 includes first layer 910, mounting layer 940 and 942 attached to the first layer, transducers 920 and 922 mounted to mounting layers 940 and 942, respectively, air gap 945 located underneath transducers 920 and 922, air gap channels 946 and 948 located between mounting layers 940 and 942, and copper pad 951. Mounting layers 940 and 942 have a u-shape. The mounting layers can be implemented by removing a portion of a PCB layer to form the u-shaped layer or by attaching a unshaped member to a layer of the PCB. In some embodiments, one or more mounting layers having positions and shapes that differ from those illustrated in FIGS. 9A-C can be implemented to support and provide an air gap underneath each transducer. FIG. 9B is a cut-away side view of monitor 900 from the perspective indicated by the arrow in FIG. 9A. FIG. 9B illustrates the monitor implemented on a PCB with transducer 920 mounted to mounting layer 940, mounting layer 940 attached to first layer 910, air gap 930 underneath transducer 920, and circuitry 960 attached to the opposite surface of the PCB. FIG. 9C is a front view illustrating the monitor 900. In the monitor of FIGS. 9A, 9B and 9C, the outer layer is removed to form an undivided air gap underneath transducers 920 and 922. The removed portion extends around the transducers to reveal portions of the underlying layer 910 not covered by the transducer elements.

As illustrated in the PCB of FIGS. 7A-B, 8A-B, and 9A-C, the transducer is mounted to the outer layer of the PCB where the transducer length slightly overlaps the air gap portion. In some embodiments, the air gap portion can be formed such that the transducer is mounted to the PCB where the transducer width slightly overlaps the air gap. In one embodiment, the width and length of the air gap portion will not be made larger than the width and length of the transducer elements. This prevents any silicone based epoxy or molten thermoplastic gel that may be applied to the transducer from getting into the air gap portion. If epoxy or gel does penetrate the air gap, the acoustic impedance of the gel and the exposed fiber glass material comprising the PCB are different enough that the ultrasound energy will still be effectively reflected towards the desired direction. Since the air gap is relatively thin, the loss of energy, if any, will be negligible.

Oil-Based Transmission Media for Ultrasonic Frequency Transmission

Figure 10A:
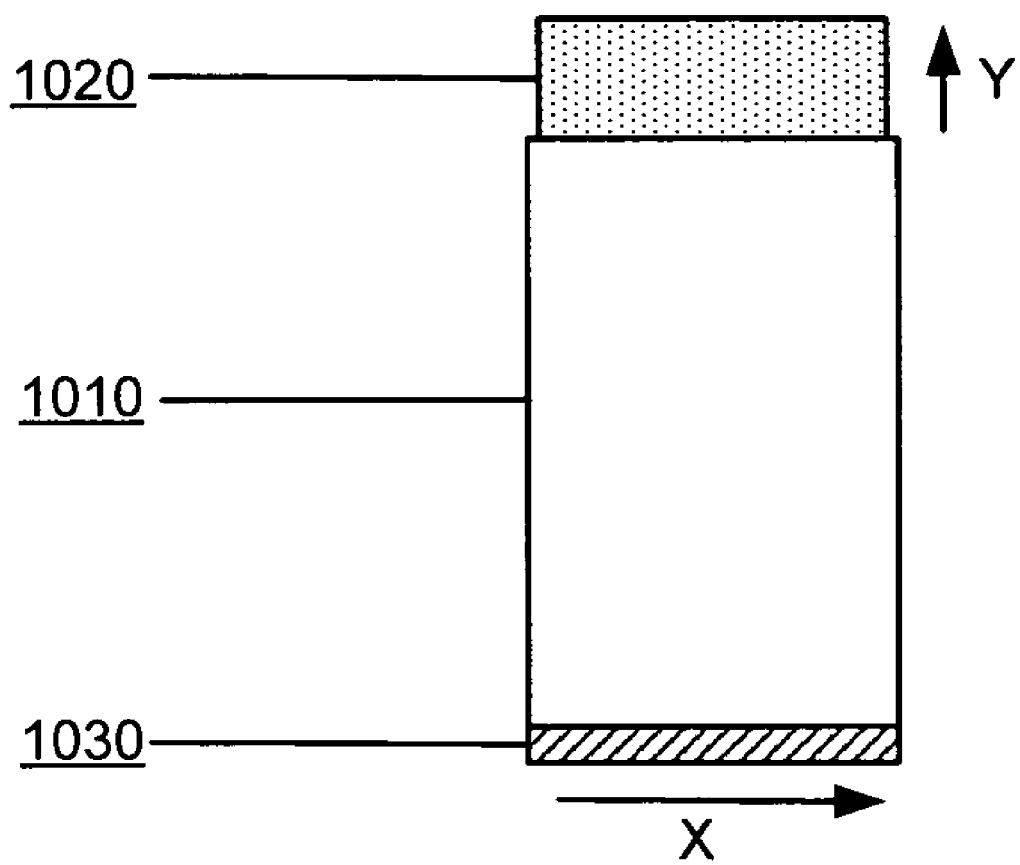
FIG. 10A illustrates one embodiment of a biocompatible oil-based transmission medium applicator.

In one embodiment, a transmission medium may be implemented as an oil based transmission medium. An oil-based transmission medium may be biocompatible, and used to transmit an ultrasonic frequency signal between an ultrasonic monitor and a subject. The biocompatible oil-based transmission medium may be in contact with the subject or a gel pad and either the transducers or a protective material. The protective material may have a surface that is directly or indirectly in contact with the transducers, such as a room temperature vulcanizing (RTV) silicone rubber layer adhesive. A protective material such as an RTV layer can be a molded material that encompasses the transducers and a portion of the PCB outer surface and is mounted to the PCB. Protective material layers in an ultrasonic monitor are discussed in more detail below. Oil-based transmission mediums are generally transparent to ultrasound. Thus, the energy loss during transmission is minimized significantly. This allows the ultrasonic monitor to effectively measure both the blood flow rate and cardiac output accurately. In some embodiments, the oil-based transmission medium may be applied directly to the ultrasonic monitor and/or the user's skin. FIG. 10 illustrates an embodiment of an oil-based transmission medium applicator 1000. Applicator 1000 includes casing 1010, oil-based transmission medium 1020, and dial 1030. Oil-based transmission medium 1020 extends from casing 1010 and can be directly applied to a surface. Dial 1030 may be rotated in a direction X as shown to force oil-based transmission medium 1020 in a direction Y as shown. Rotating dial 1030 allows additional oil-based transmission medium to be exposed from casing 1010 and applied to a user or ultrasonic monitor. Applicator 1000 is one example of many possible types of oil-based transmission medium applicators. Other types of applicators can be used with the oil-based transmission medium discussed herein as well.

Biocompatible oil-based transmission mediums consist primarily of a wax component and an oil component. The amounts of these components may determine whether the biocompatible oil-based transmission medium has a balm-like or lotion-like composition. Both balm and lotion-like transmission mediums may transmit ultrasonic frequency signals, but the different consistencies may be better suited for different uses. For example, a balm-like transmission medium may be well-suited for applicators such as applicator 1000 of FIG. 10, while a lotion-like transmission medium may be better suited for application from a lotion dispensing container. Both balm-like and lotion-like oil based transmission mediums are easy to apply, easy to clean and may be reapplied as often as required. A balm-like oil-based transmission medium may be used as encapsulating moldings over a portion of the ultrasonic monitor. This is discussed below.

In one embodiment, a wax component of an oil-based transmission medium may be comprised of a natural low melting wax. Examples of natural low melting waxes include beeswax, carnauba wax, and candelilla wax, etc Beeswax has a melting point of about 62°-65° C., carnauba wax has a melting point from 82-83° C., and candelilla wax has a melting point from 68-73° C. In one embodiment, any low melting wax may be used which has a melting point between 37-90° C. In some embodiments, FDA approved fully-refined paraffin waxes and microcrystalline waxes having a melting point within this given range can also be used as a total or partial substitute of a wax component.

The oil component of an oil-based transmission medium may be a natural oil, such as a plant based oil. Plant based oils are extracted or squeezed from their corresponding plants, flowers or fruits, or may be a mixture of several fatty acid esters. This process is well known in the art. Examples of suitable natural oils for an oil-based transmission medium include almond oil, aloe vera oil, apricot kernel oil, avocado oil, calendula oil, evening primrose oil, grape seed oil, hazelnut oil, jojoba oil, macadamia oil, olive oil, pumpkin seed oil, rose hip oil, safflower oil, sesame oil, sunflower oil, walnut oil, wheat germ oil, canola oil, coconut oil, tea tree oil, and vitamin E oil. In some embodiments, natural oils suitable for use in an oil-based transmission medium need not be liquids at room temperature, but may have a butter-like consistency instead. Examples of butter-consistency natural oils include coconut butter, cocoa butter, jojoba butter, shea butter, most hydrogenated oils and lanolin. In some embodiments, some highly refined petroleum based oils, such as mineral oil and petrolatum, can be used as partial substitutes for plant based oils.

In addition to the wax and oil components, some amount of an "essential oil" can be added to the oil-based transmission medium. In one embodiment, an essential oil is an oil or other extract from a plant that is scented, aromatic, acts as a moisturizer, or repairs skin damage. Examples of essential oils may include bay leaf, bergamot, caraway, cardiman, cedar, citronella, eucalyptus, frankincense, gardenia, juniper, orange, patchouli, rosemary, and tea tree oil. Essential oils may be used to add fragrance, provide healing effects, moisturize, change the oil consistency or provide some other feature to the biocompatible oil based transmission medium.

An oil-based transmission medium may also include some amount of water. Most natural waxes due to their acidity can be partially soluble in water. The water may be used to soften the transmission medium composition and provide a jelly or cream-like consistency. The addition of a water component in an oil-based transmission medium will not affect the biocompatibility of the transmission medium. An oil-based transmission medium having a jelly or cream-like consistency is well suited to be applied to the subject and/or the ultrasonic monitor from a lotion or cream applicator.

Figure 11A:
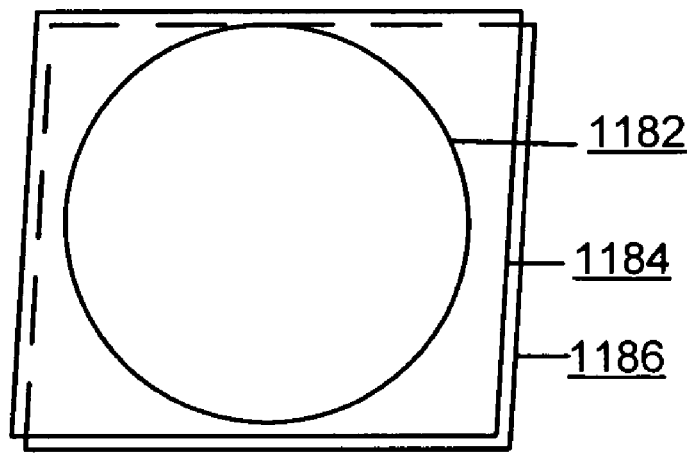
FIG. 11A illustrates one embodiment of a perspective view of a oil-based transmission medium component.
Figure 11B:
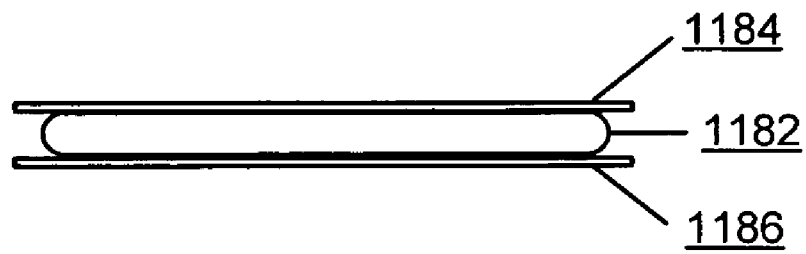
FIG. 11B illustrates one embodiment of a side view of a oil-based transmission medium component.

The ratio of wax and liquid (liquids such as oil and water) in an oil-based gel that is biocompatible with a user's skin can vary. In one embodiment, a wax to liquid ratio of about 1:1 to 1:3 produces a material having a soft, solid-like consistency that maintains a fixed shape. In one embodiment, the fixed shape may be a disc, a rod or some other shape that can be positioned between an ultrasonic monitor and the user's skin. An example of a disc shaped transmission medium is illustrated in FIGS. 11A and 11B and discussed in more detail below. A transmission medium of this type, having a soft but solid-like consistency, may be pliable upon rubbing onto the skin and feel dry with these compositions. A fixed shape oil-based transmission medium may be used as encapsulating moldings over a portion of the ultrasonic monitor. This is discussed in more detail below.

An oil-based transmission medium having a wax to liquid ratio of about 1:4 has the consistency of a jelly, similar to a Vaseline or petrolatum material. If the ratio is increased to between 1:6 and 1:10, the oil based transmission medium may have a consistency of a cream or lotion. An example of a device for applying an oil-based transmission medium having a wax-liquid ratio between 1:1 and 1:10 is illustrated in FIG. 10. Regardless of the consistency of the oil based transmission medium, it may act as an effective ultrasound transmission medium between the ultrasonic monitor and the skin of a user. In one embodiment, the oil based transmission medium to be used with an ultrasonic monitor may be between 1:1.5 to 1:4, such that the transmission medium composition has a dry feel and is not too messy to apply. An oil-based transmission medium having a cream or lotion-like consistency is well suited to be applied to the subject and/or the ultrasonic monitor from a lotion or cream applicator.

As discussed above, the ratio of wax to liquid in the oil based transmission medium may determine whether the consistency of the transmission medium is lotion-like or balm-like. For a lotion-like transmission medium, the transmission medium may be characterized by its viscosity property. The viscosity may be determined by the standard ASTM D2196. This standard determines the viscosity of coatings and related materials by measuring the torque on a spindle rotating at a constant speed within the material. In one embodiment, a Brookfield RVF viscometer may be used to determine the viscosity characteristic using the ASTM D2196 standard. Using this standard, the apparent viscosity may be determined as:

$$V=fs,$$

where, V is the viscosity of the sample in centipoises (mPa s), f is the scale factor furnished with the instrument, and s is the scale reading of the viscometer.

In one embodiment, a suitable ultrasound transmission lotion-like oil-based transmission medium may have a viscosity between 5,000 to 2,000,000 centipoises. In another embodiment the viscosity may be between 20,000 and 2,000,000 centipoises. In yet another embodiment, a suitable ultrasound transmission lotion oil based transmission medium has a viscosity between 100,000 and 2,000,000 centipoises.

Oil based transmission mediums having a balm-like consistency can be characterized by melting point and consistency. The melting point can be determined using the standard ASTM D-127. In one embodiment, the final melting point of the composition is preferably between 50°-75° C. The standard ASTM D-127 determines the drop melting point of the petroleum wax. According to this standard, specimens are deposited onto thermometer bulbs by dipping chilled thermometers into the sample of the material. The thermometers bearing the specimens are then placed in test tubes and heated by means of a water bath until the specimen melts and the first drop falls from each thermometer bulb. The average of the temperatures which these drops fall is the drop melting point of the sample.

Consistency of an oil-based transmission medium may be characterized by cone penetration according to standard ASTM D-937, measured with a standard cone. The unit for the cone penetration is recorded in 0.1 millimeter. The cone penetration for a balm-like oil based transmission medium of the present invention may be between 30-240 and preferably between 50-200. In yet another embodiment, the cone penetration is between 60-120. Cone penetration measurement according to ASTM D-937 involves melting the sample, heating the sample to 82° C. and then cooling the sample under controlled conditions to 25° C. Penetration of the samples is then measured with a cone of standard dimensions. While at the desired temperature, a Penetrometer is used to apply the standard dimension cone to the sample for five seconds under a load of 150 grams. The depth of the penetration of the cone is used as a measure of the sample consistency.

In one embodiment, an oil based transmission medium of the present invention may be implemented using commercial products. These commercial products include lip balm, lip stick, Vaseline, petroleum and other similar products.

Gel Pad with Membrane Layer

In one embodiment, the transmission medium may be implemented as a gel pad having a membrane layer. A gel pad can be used to transmit the ultrasonic frequency signal between the ultrasonic monitor and the subject. The gel pad may be in contact with the subject or an oil based transmission medium, and either the transducers or a surface of a protective material that is directly or indirectly in contact with the transducers, such as an protective layer (discussed in more detail below). Gels having high oil content are generally transparent to ultrasound. Thus, the energy loss during transmission is minimized significantly. This allows the ultrasonic monitor to effectively measure both the blood flow rate and cardiac output accurately.

Figure 10B:
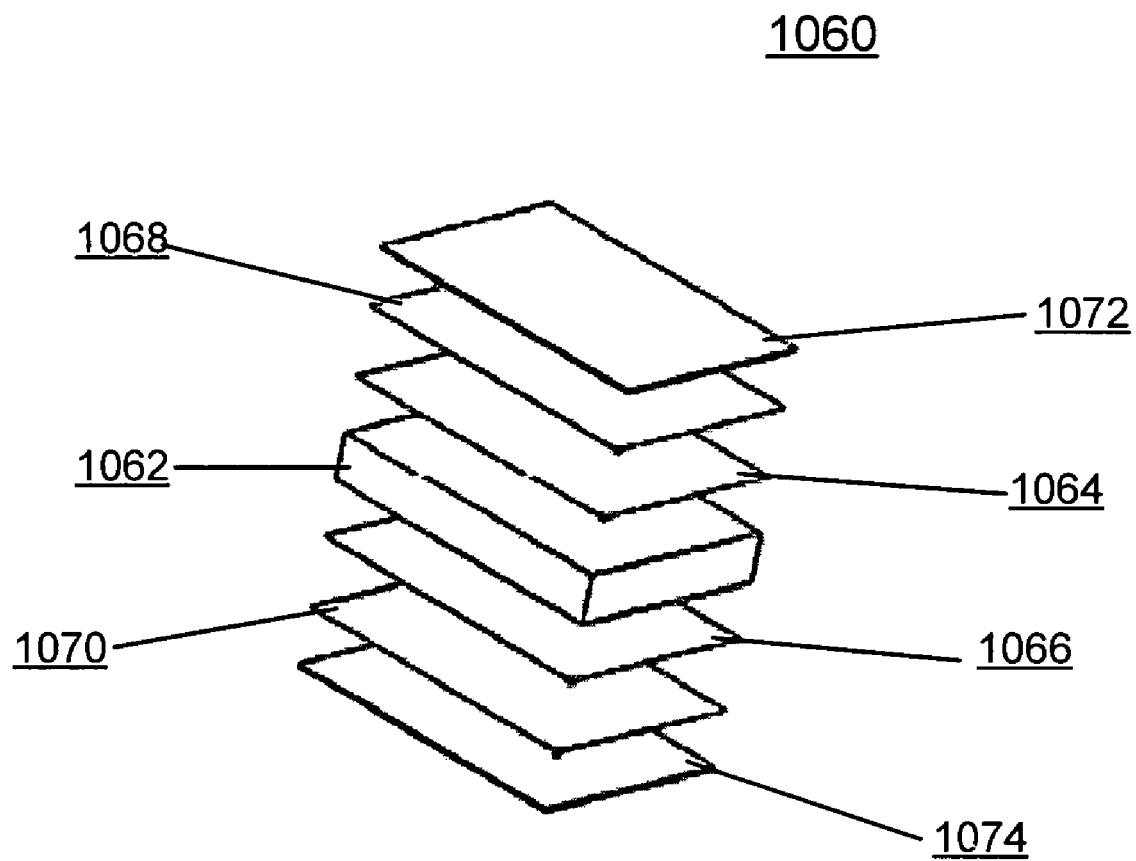
FIG. 10B illustrates one embodiment of a gel pad.

In one embodiment, the gel pad may be implemented as a gel pouch. FIG. 10B illustrates one embodiment of a gel pouch. Gel pouch 1060 includes a gel layer 1062, primer layers 1064 and 1066, membrane layers 1068 and 1070, and adhesive layers 1072 and 1074. The gel layer 1062 is the primary transmitting medium of the gel pouch. The primer layer can be applied to the surface of the gel layer. In an embodiment wherein the gel layer is generally shaped to have a top and bottom surface, a primer layer may be applied as an upper primer layer 1064 and/or a lower primer layer 1066. A membrane layer is attached to the gel layer via the primer layer. The membrane layer serves to aid in the handling of softer gels and prevents diluents from making contact with the subject's skin. Upper membrane layer 1068 is attached to upper primer layer 1064 and lower membrane layer 1070 is attached do lower primer layer 1066. The membrane layer can be applied to one or more surfaces of the gel layer. An adhesive layer may then be applied to the outer surface of the membrane layer. The adhesive is used to attach the gel pouch to the subject's skin, the transducer, or a protective material such as an RTV element in contact with the transducer. The adhesive may also eliminate any air pockets that may exist between the gel pouch and other surfaces. An upper adhesive layer 1072 may be applied to upper membrane layer 1068 and a lower adhesive layer 1074 may be applied to lower membrane layer 1070.

Several types of materials can be used in constructing the gel pad of the present invention. The gel layer of the gel pad (gel 1062 of FIG. 10B) may be constructed of thermoplastic gel, themoset gel, hydrogels, or other similar materials. A thermoplastic gel is generally made of a thermoplastic elastomer with a large proportion of interdispersed diluent. Thermoplastic elastomers include block copolymers such as styrene-butadiene-styrene, styrene-isoprene-styrene, styrene/ethylene-co-butylenes/styrene, and styrene/ethylene-co-propylene/styrene. The styrene end blocks form glassy domains at room temperature. The glassy domains act as physical crosslinks that provide the elastomeric properties of the polymer. During heating above the glass transition temperature of styrene, i.e., about 100° C., the glassy domains melt and the polymers revert to a liquid state. During cooling, the glassy domains re-form again. Hence, the process is reversible. Other block copolymers, such as ethylene-(ethylene-co-butylene)-ethylene copolymers which contains crystalline polyethylene end blocks, can also be used to prepare thermoplastic gels.

A thermoset gel, such as a polyurethane or silicon gel, is generally made of a chemically bonded three-dimensional elastomeric network which entraps a large amount of low volatility liquids or diluents. The elastomeric network is permanent and cannot be reversed to a liquid state through heating. A certain amount of diluent is necessary in order to ensure good conformability of the gel to the skin and low attenuation for ultrasound transmission while still maintaining the load bearing properties. The gel can be used at a temperature that ranges from −30° C. to +70° C., wherein the gel maintains its shape and load-bearing elastic properties.

Thermoset and thermoplastic gels invariably contain a large percentage of diluents entrapped in an elastomeric network. When properly formulated, these gels are stable and can resist stress or temperature cycling. The stability is governed by thermodynamic factors such as the crosslink density of the elastomeric network and the compatibility of the diluents with the elastomeric network. However, even with a thermodynamically stable gel, when brought in contact with skin, the diluents in the gel can still diffuse out and enter the living subject. This is due to the fact that there is a concentration gradient of the diluents across the skin; the natural tendency for the diluents is to migrate out of the gel, where the concentration of the diluents is high, and into skin, where the initial concentration of diluents is zero. The diffusion is thus kinetically controlled by the Fick's Law. The diffusion of diluents, particularly silicone oil, may have a deleterious effect to the living. In one embodiment, the diffusion of the diluents is prevented by adhering or laminating a compliable barrier membrane to the gel layer.

Hydrogels can consist of a water soluble polymer such as polyacrylic acid, polyacrylamide, poly (acrylic acid-co-acrylonitrile), poly(acrylamide-co-acrylonitrile, etc. They are dissolved in a large amount of water, approximately 50% to 98% by weight of the total mixture. The mixtures are optionally thickened by ions such as sodium, zinc, calcium, etc., which are provided by adding the corresponding metal salts. When used with a membrane, the membrane can effectively seal the mixtures to prevent the water evaporation or migration.

The membrane layer may be made of a thin film of polyurethane, silicone, poly(vinyl chloride), natural or synthetic rubbers, polyester, polyamides, or polyolefins which include low density polyethylene, plastomers, metallocene olefin copolymers, or other similar materials. In fact, any thin polymer film that is pliable and conformable is within the scope of this invention. Those skilled in the art can determine a suitable membrane material depending on the gel material selected. The membrane can be laminated to the gel pad using an adhesive. The membrane can also be formed by spraying of coating a film forming liquid such as a polyurethane elastomer solution, or latex onto the surfaces of the gel layer. Upon drying of the liquid, a thin membrane is formed which can achieve the same result as the laminating process. Depending on the type of diluents in the gel layer, a membrane is selected to give the best barrier effect. The membrane is preferably as thin and soft as possible so that it complies to the skin well and minimizes the possibility of air entrapment. The membrane also provides for easier gel pad handling, reduced dirt accumulation, and easier cleaning.

Several types of adhesives and primers may be used to generate the gel pouch of FIG. 10B. For example, Automix™ Polyolefin Adhesion Promoter 05907 by 3M™ and LOC-TITE™ 770 Polyolefin Primer by Loctite can be used as a primer between the gel layer and membrane layer. AROSET™ 3250 pressure sensitive adhesive by Ashland Specialty Chemical Company can be used as the adhesive between a membrane layer and the subject's skin. DOW CORNING 7657 Adhesive used with SYL-OFF 4000 Catalyst by Dow Corning™ may be used as an adhesive between the membrane layer and an RTV element.

The pressure sensitive adhesive applied to the outer surface of the membrane layer can be rubber, silicone or acrylic based depending on the based material of the gel. For example, if thermoplastic gel is used, a rubber based pressure sensitive adhesive will provide better adhesion. It is also preferable that the pressure sensitive adhesive is medical grade that does not cause skin sensitization. If a membrane is in direct contact with the skin, it is also desirable that the membrane itself does not cause skin sensitization. Some membrane materials made of natural rubber latex are known to cause allergic reaction to the skin of some people.

In another embodiment, the gel pad may consist of a single layer of thermoplastic gel material. This is particularly convenient if a biocompatible fluid such as medical grade mineral oil is used as the diluent in the gel. Such oil, if migrates into the skin, does not cause adverse effect to the living tissues. For example, baby oil, a medical grade mineral oil, may be used for the diluent. In this case, the thermoplastic gel material is compliant enough to the surface of the subject such that no adhesive is needed between the gel pad and the subject's skin. In particular, when applied with a slight amount of pressure, such as that applied by a wrist-worn ultrasonic monitor with a wrist-strap, any existing air pockets are generally eliminated. Minimum adhesion is required to keep the single layer thermoplastic gel pad in place when in contact with the ultrasonic monitor and a subject's skin. This is advantageous because it is simple, inexpensive to construct and allows a large number of adhesives to be used to keep the gel pad in contact with a protective layer, such as RTV material. In one embodiment, the gel may have a thickness of between about 1 and 10 millimeters. In some embodiments, the gel may have a thickness between 1 and 5 millimeters.

FIG. 11A illustrates a top view of one embodiment of a transmission medium component 1180. Transmission medium component 1180 may be implemented as gel pad having a membrane, an oil-based transmission medium, or some other material. Transmission medium component 1180 includes transmission medium 1182, first cover 1184 and second cover 1186. FIG. 11B illustrates a side view of transmission medium component 1180. In the embodiment illustrated, transmission medium 1182 has a flat disk-like shape. In some embodiment, transmission medium 1182 may have a rectangular shape, cylindrical shape, or some other shape. The covers are applied to the transmission medium during manufacturing and protect it until it is used. The covers can be constructed of wax paper or some other type of material.

Covers 1184 and 1186 are removed before use of transmission medium 1182. Transmission medium 1182 is then applied to the area between the ultrasonic monitor and the subject's skin. In one embodiment, wherein the monitor is worn on the wrist, transmission medium 1182 is applied between the wrist worn monitor and the subject's wrist. In one embodiment, the monitor includes a recess constructed in its outer surface that is positioned towards the subject. Transmission medium 1182 can be applied to the recessed area on the monitor to help keep it in place. When transmission medium 1182 includes a pressure sensitive adhesive and is compressed between the monitor and the subject, it may adhere to both the monitor and the subject. Transmission medium 1182 may be compressed when the monitor is strapped to a subject, held in place without a strap for a period of time, or in some other manner that straps, fastens or otherwise applies the monitor to the subject.

Figure 12A:
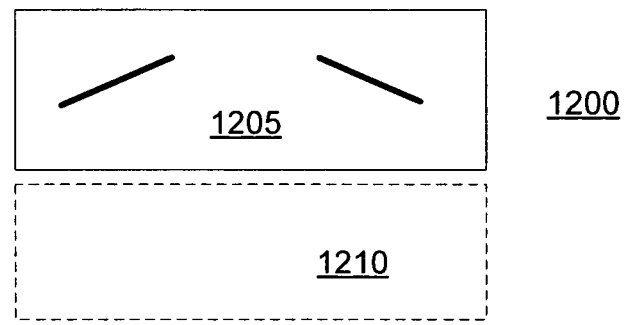
FIG. 12A illustrates one embodiment of a transmission medium configuration.
Figure 12B:
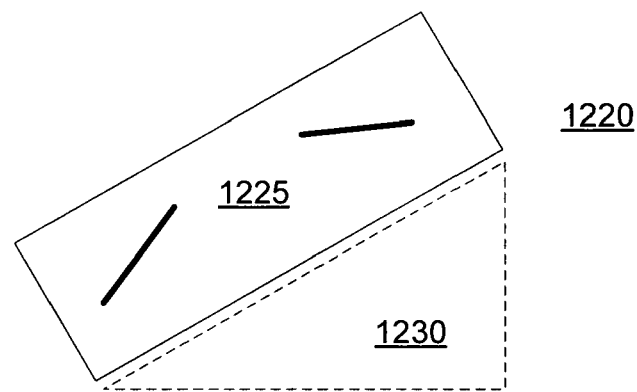
FIG. 12B illustrates one embodiment of a transmission medium configuration.
Figure 12C:
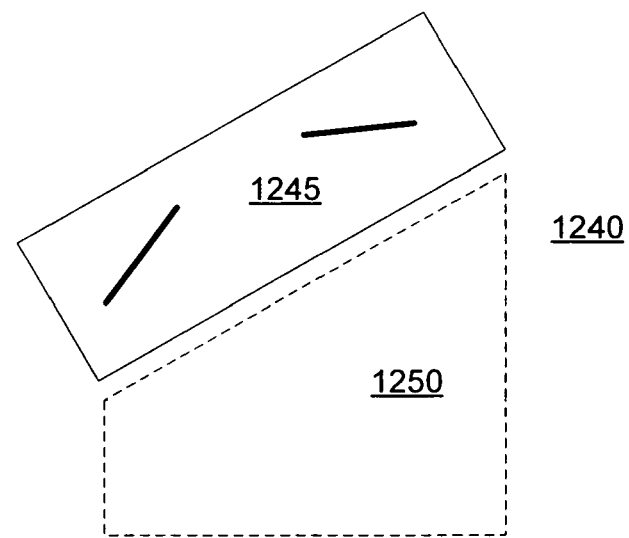
FIG. 12C illustrates one embodiment of a transmission medium configuration.

The transmission medium shape and thickness can be designed to allow ultrasonic monitors to operate at different bias angles. Ultrasonic monitor 1200 of FIG. 12A illustrates a monitor module 1205 in contact with a transmission medium 1210 having a rectangular cross section. Ultrasonic monitor 1220 of FIG. 12B illustrates a monitor module 1225 in contact with transmission medium 1230 having a triangular cross section. Ultrasonic monitor 1240 of FIG. 12C illustrates a monitor module 1245 in contact with transmission medium 1240 and FIG. 12C having a trapezoidal cross section. Transmission mediums 1210, 1230 and 1240 may be comprised of a gel having a membrane layer, an oi-based gel, or some other material. The dimensions of these transmission medium shapes are based on the desired bias angle and the depth of the moving object to be detected.

The transmission medium may be used with an ultrasonic monitor in several ways. In one embodiment, a transmission medium can be heated to a molten state and over-molded onto the transducer or the plastic housing of the ultrasonic monitor. Oil-based transmission media having a fixed or balm-like consistency are well suited for over-molding. Though the oil-based transmission medium will adhere to the transducer or the plastic housing, an adhesive may be used to ensure a durable bond. Adhesives suitable for over-molding include EC6000 by ECLECTRIC PRODUCTS, Inc.

In another embodiment, a protective layer may be positioned between the transducers and the transmission medium. The transmission medium is positioned between the protective layer and the subject. The protective layer may be molded such that it encompasses the transducers and a portion of the PCB outer surface. In one embodiment, the mold is mounted to the PCB. The protective layer material is then placed into the mold. Though the protective layer will adhere to the exposed PCB surface within the mold, an adhesive may be used to further secure the protective layer material to the PCB. A suitable protective layer material can provide excellent ultrasonic signal transmission and is firmer than a natural oil-based transmission medium. The firmness of the suitable protective layer material can prevent damage to the transducer elements due to contact from the oil-based transmission medium and other objects.

In one embodiment, the protective layer may be comprised of a room temperature vulcanizing (RTV) silicone rubber layer adhesive. RTV silicones, which are used to encapsulate and protect transducers, can be substituted with other types of materials so long as they provide adequate mechanical strength, exhibit minimum impedance to ultrasound, and can be applied easily and with the least entrapped air bubbles.

Suitable substitutes for RTV silicones may be materials such as include flexible epoxy, elastomeric polyurethane, flexible acrylic, etc. RTV silicone substitutes can be single or two component systems. These substitutes are preferably applicable as solvent-free liquids, and can be crosslinked at room temperature without using heat. The crosslinking can be achieved by chemical reactions, moisture cured mechanisms, or ultra violet light. An example of a suitable RTV replacement material may include Eccobond 45 with catalyte 15, provided by Emerson Cuming of Billerica, Mass. Eccobond 45 with Catalyst 15 is a black, filled epoxy adhesive which, by varying the amount of catalyst used, can adjust the hardness from flexible to rigid. It has an easy mix ratio range and bonds well to a wide variety of substrates. Other examples of RTV substitute materials may include Stycast U2516HTR (a flexible polyurethane casting resin) and Stycast 1365-65N (a flexible epoxy "gel" encapsulant), also provided by Emerson Cuming.

Figure 13A:
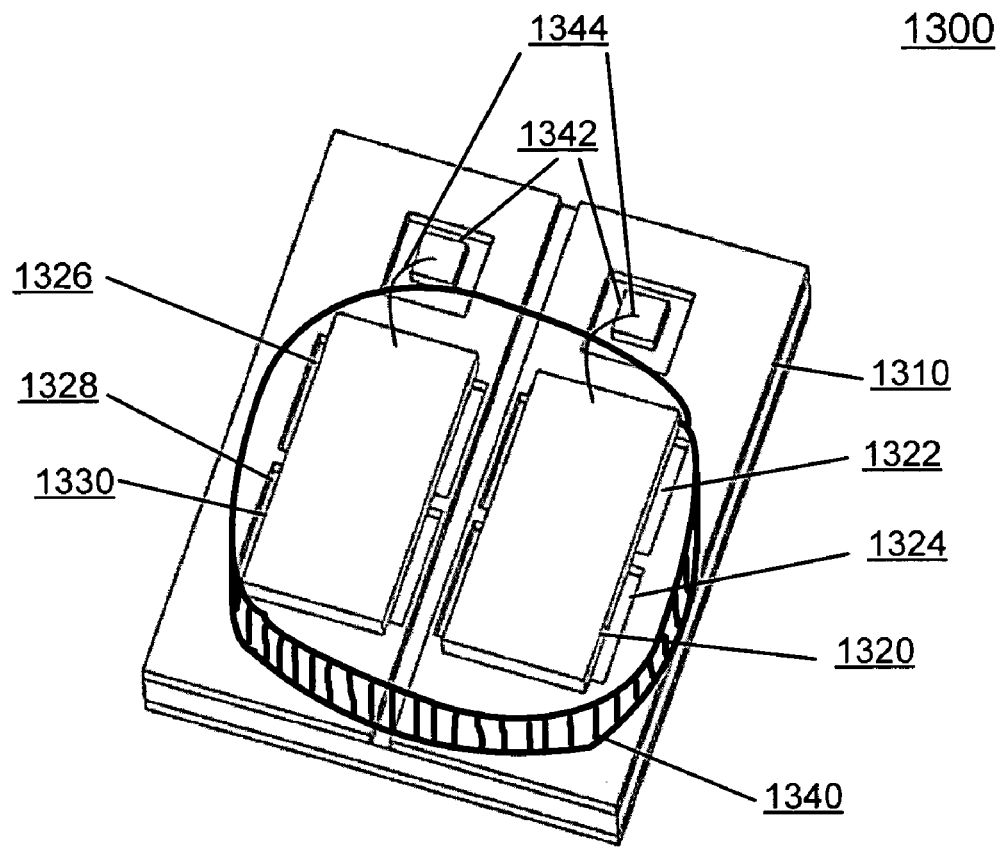
FIG. 13A illustrates one embodiment of a perspective view of an ultrasonic monitor on a PCB with a mold.
Figure 13B:
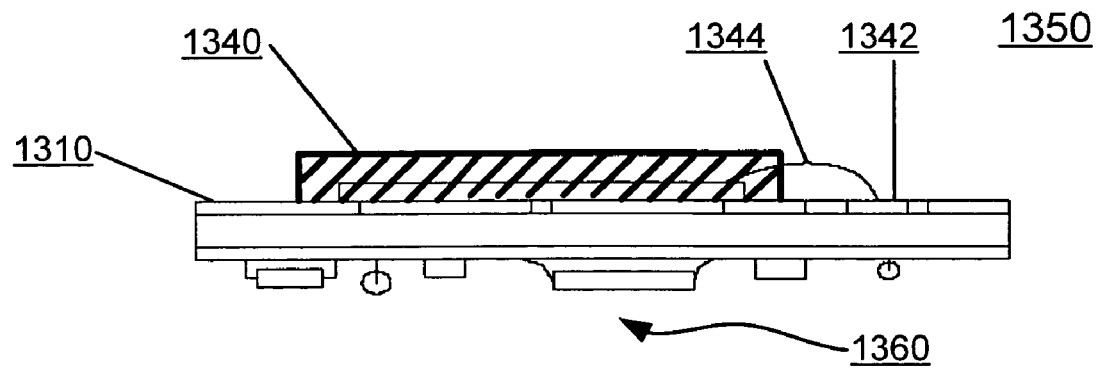
FIG. 13B illustrates one embodiment of a side view of an ultrasonic monitor on a PCB with a mold.

An embodiment of a PCB system that incorporates a molded protective layer is shown in FIGS. 13A and 13B. The monitor of system 1300 in FIG. 13A includes an outer layer 1310 of a PCB, transducers 1320 and 1330 mounted to the outer layer, protective layer mold 1340, copper contact points 1342, connecting wires 1344 that connect copper contact points 1342 to transducers 1320 and 1330, air gap portions 1322 and 1324 underneath transducer 1320 and air gap portions 1326 and 1328 underneath transducer 1330. FIG. 13B illustrates a side view of the PCB system and further illustrates circuitry 1360 used to implement the monitor that is mounted to the opposite surface of the transducers. Protective layer mold 1340 is constructed such that it encompasses the transducers, air gap portions, and a portion of the outer layer of the PCB. When the protective layer is poured, injected or otherwise placed within mold 1340, the protective layer will cover the transducers, air gap portions and the portion of the outer layer of the PCB encompassed by mold 1340. Connecting wires 1344 may be located over or under mold 1340. Mold 1340 may be implemented as a solder mold and attached to the PCB using appropriate adhesives as discussed above. The protective material is placed into mold 1340 during production. The oil-based transmission media may then be attached to the protective material layer using an appropriate adhesive.

In one embodiment, the oil-based transmission medium can be molded over the protective material. The outer surface of the oil-based transmission medium can then be placed in contact with a subject's skin. An adhesive may optionally be applied to the outer surface of the oil-based transmission medium in contact with a subject's skin. Oil-based transmission media having a fixed or balm-like consistency are well suited for over-molding onto a protective material layer.

The protective material can be selected such that it acts as a mechanical isolator between the transducers and outside forces. The protective material absorbs outside forces, such as contact or pressure from a subject's skin, and prevents them from affecting the resonating frequency of the transducers. A protective material formed of RTV may be constructed from several types of materials, including Silastic™ E RTV Silicone Rubber and DOW CORNING 3110, 3112 and 3120 RTV rubbers, all by DOW CORNING™. DOW CORNING™ 1301 primer and other similar primers may be used to attach the RTV material to the PCB.

As discussed above, a transmission medium, protective layer, or both may be positioned directly or indirectly between the transducer elements and a subject. In some embodiments, an additional substance may be placed between the transmission medium and/or protective layer and the subject being monitored. For example, an oil, such as baby oil or mineral oil, may be applied between the subject and the transmission medium or protective layer. This can help eliminate small air pockets between the transmission medium or protective layer and the subject. Other substances can be used for this purpose as well, including water, waxes and creams as discussed herein and other similar substances as will be understood by those skilled in the art.

Encapsulated Ultrasonic Monitor

In one embodiment of the present invention, the ultrasonic monitor can be encapsulated to make it water resistant. The ultrasonic monitor can be sealed using an ABS plastic material, gel material, or both. For instance, the electronic component side can be sealed in ABS plastic material while the transducer side is sealed by a softer gel material such as a natural oil-based transmission medium. Oil-based transmission media having a fixed or balm-like consistency are well suited for over-molding. In another embodiment, both the transducer side and the electronic component side can be sealed using an ABS plastic material.

In some embodiments, the sealed assembly can be formed with a recessed portion located over the transducers or an protective layer portion of the ultrasonic monitor. An oil-based transmission medium may be positioned at the recessed area to provide ultrasonic signal transmission. Placing the oil-based transmission medium at the recessed portion will help maintain the position of the oil-based transmission medium at the location of the recessed portion and over the transducers. The transmission medium illustrated and discussed in reference to FIGS. 11A-B can be used in this embodiment. In some embodiments, the resulting assembly can be further molded or mechanically coupled in some way to a polyurethane based wristwatch strap. Both final assemblies will be waterproof and retain good ultrasonic transmission properties with a subject.

Figure 14A:
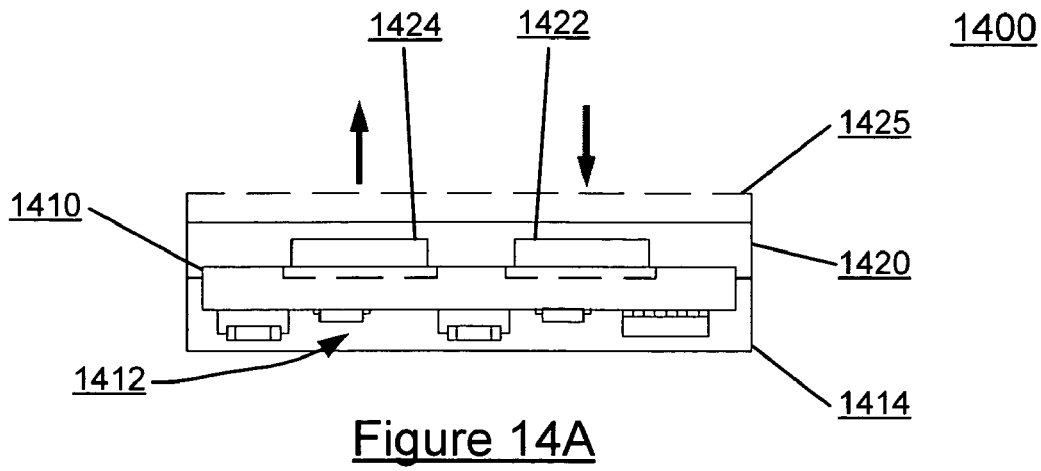
FIG. 14A illustrates one embodiment of a side view of an encapsulated PCB board.

FIG. 14A illustrates an embodiment of a sealed ultrasonic monitor 1400. Monitor 1400 includes PCB 1410, circuitry 1412, plastic housing 1414, protective layer 1420, transducers 1422 and 1424 and transmission medium 1425. In one embodiment, protective layer 1420 may include RTV silicon rubber or a suitable replacement material, epoxy, or a combination of these materials. PCB 1410 and circuitry 1412 are molded and sealed in plastic (such as ABS plastic) housing 1414. Protective layer 1420 is molded or cast over the transducers and sealed against the plastic housing. Transmission medium 1425 is then positioned over protective layer 1420.

Figure 14B:
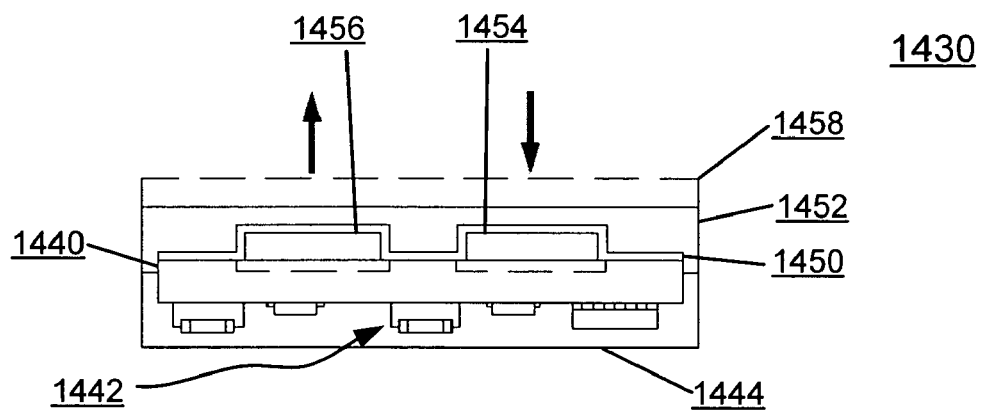
FIG. 14B illustrates one embodiment of a side view of an encapsulated PCB board.

FIG. 14B illustrates an embodiment of a sealed ultrasonic monitor 1430. Monitor 1430 includes PCB 1440, circuitry 1442, plastic housing 1444, adhesive layer 1450, protective layer 1452, transducers 1454 and 1456 and transmission medium 1458. Monitor 1430 is similar to monitor 1400 except that adhesive layer 1450 is applied between protective layer 1452 and transducers 1454 and 1456 and PCB 1440.

Figure 14C:
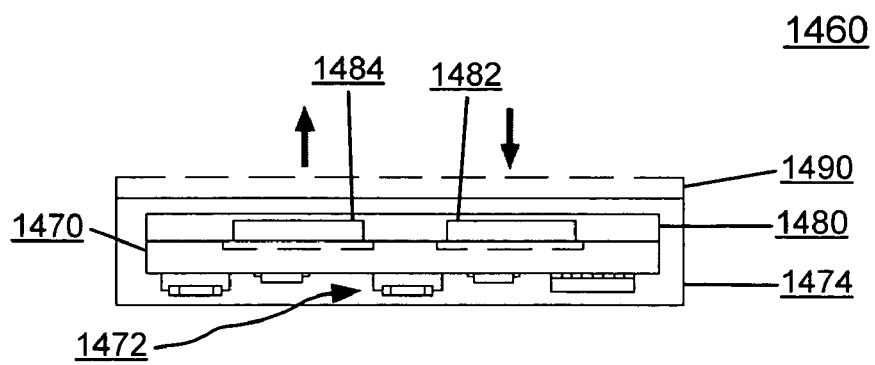
FIG. 14C illustrates one embodiment of a side view of an encapsulated PCB board.

FIG. 14C illustrates an embodiment of a sealed ultrasonic monitor 1460. Monitor 1460 includes PCB 1470, circuitry 1472, plastic housing 1474, protective layer 1480, transducers 1482 and 1484 and transmission medium 1490. Protective layer 1480 is applied over transducers 1482 and 1484. Plastic housing 1474 encapsulates the entire ultrasonic monitor, including protective layer 1480, PCB 1470 and circuitry 1472. Transmission medium 1490 is in contact with a surface of plastic housing 1474 closest to transducers 1482 and 1484.

Figure 15A:
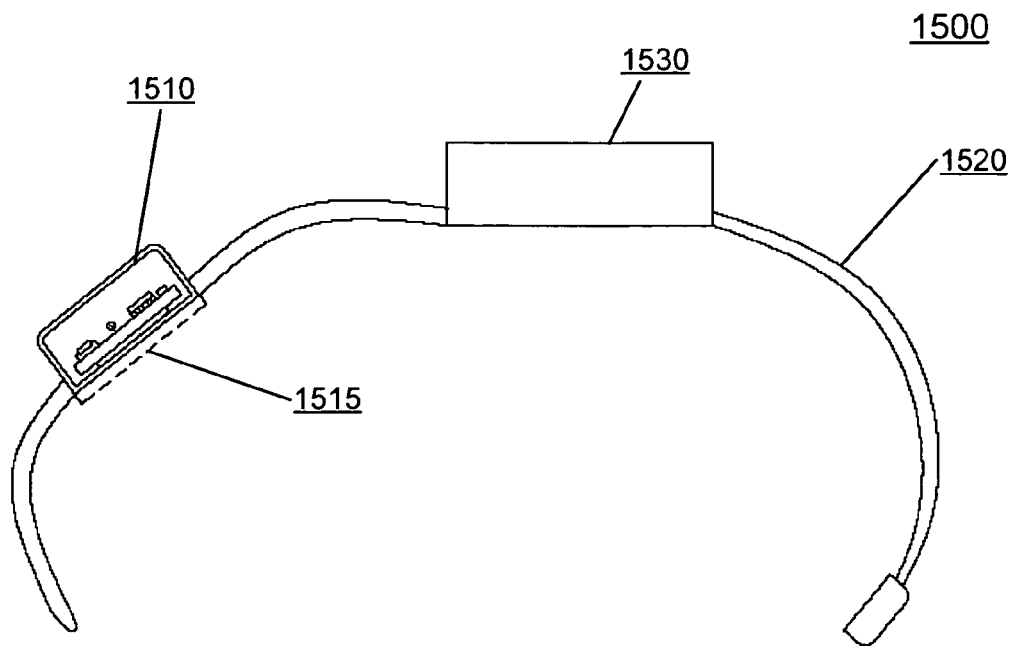
FIG. 15A illustrates an embodiment of an ultrasonic monitor system with an encapsulated transmission medium.

An encapsulated ultrasonic monitor may be used with a permanently attached or disposable transmission medium. The transmission medium may be oil based, a gel pad, or a combination of the two. The disposable transmission media can be attached on a recessed area of a surface of the ultrasonic monitor. An embodiment of a wrist worn ultrasonic monitor 1500 that is encapsulated in a housing is illustrated in FIG. 15A. Monitor 1500 includes ultrasonic monitor module 1510, transmission medium 1515 attached to ultrasonic monitor module 1510, display device 1530, and strap 1520 attached to the display device and monitor module. Transmission medium 1515 is attached to ultrasonic monitor module 1510 during production. In one embodiment, the transmission medium can be attached to the monitor module 1510 though a molding process. Fixed or balm-like consistency biocompatible oil based transmission mediums are well suited for attachment to ultrasonic monitor module 1510.

Figure 15B:
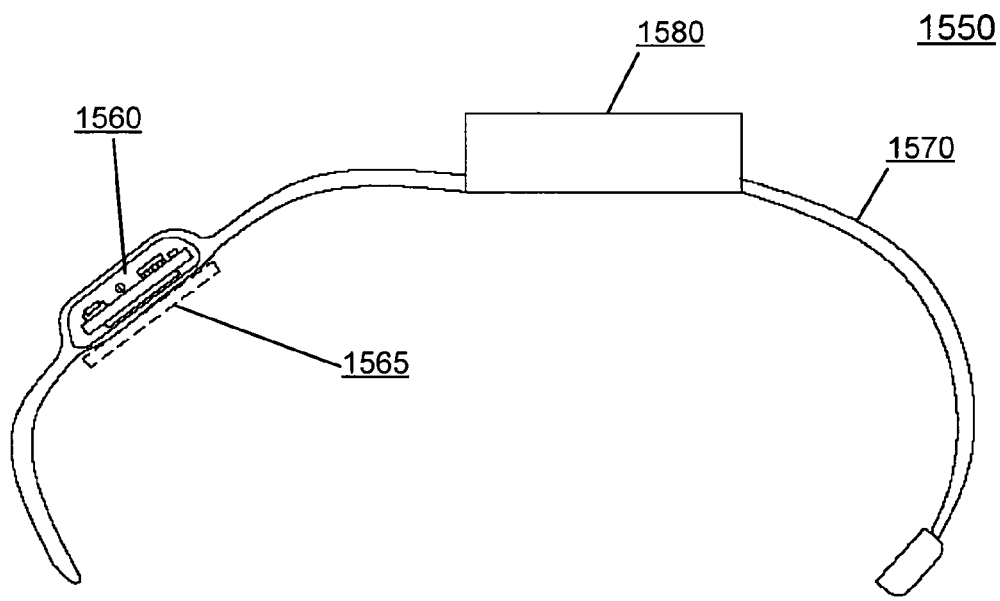
FIG. 15B illustrates an embodiment of an ultrasonic monitor system with an attached transmission medium.

One embodiment of a wrist worn ultrasonic monitor 1580 that is encapsulated in a housing is illustrated in FIG. 15B. Monitor 1580 includes ultrasonic monitor module 1560, disposable transmission medium 1565 attached to monitor module 1560, display device 1580, and strap 1570 attached to the display device and monitor module. The disposable transmission medium 1565 can be attached to the monitor module just before the monitor is used. Fixed or balm-like consistency biocompatible oil based transmission media are well suited for use as disposable oil-based transmission medium 1565. Ultrasonic monitor modules 1510 and 1560 contain slightly different shapes. This is for purposes of example only. The shapes of ultrasonic monitor modules of FIGS. 15A and 15B are interchangeable and are not intended to limit the scope of the present invention.

The foregoing detailed description of the invention has been presented for purposes of illustration and description. It is not intended to be exhaustive or to limit the invention to the precise form disclosed. Many modifications and variations are possible in light of the above teaching. The described embodiments were chosen in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

We claim:

1. An ultrasonic monitor comprising:
    an ultrasonic monitor module attached to a wrist strap, the wrist strap is adapted to be worn around a wrist of a subject, and the ultrasonic monitor module has a surface which faces the wrist;
    an ultrasonic transmitter and an ultrasonic receiver provided and sealed within the ultrasonic monitor module; and
    a biocompatible oil-based transmission medium positioned in contact with the surface of the ultrasonic monitor module and with skin of the subject's wrist, and providing transmission of ultrasonic signals between the ultrasonic monitor module and the subject's wrist, the biocompatible oil-based transmission medium consists of natural wax and oil.

2. The ultrasonic monitor of claim 1, wherein the oil is a natural oil which is one or more of almond oil, aloe vera oil, apricot kernel oil, avocado oil, calendula oil, evening primrose oil, grape seed oil, hazelnut oil, jojoba oil, macadamia oil, olive oil, pumpkin seed oil, rose hip oil, safflower oil, sesame oil, sunflower oil, walnut oil, wheat germ oil, canola oil, coconut oil, tea tree oil, and vitamin E oil.

3. The ultrasonic monitor of claim 1, wherein a ratio of the wax to a liquid in the biocompatible oil-based transmission medium, the liquid includes the oil, is between 1:1 and 1:3 so that the biocompatible oil-based transmission medium has a consistency of a balm.

4. The ultrasonic monitor of claim 1, wherein the surface is in a recessed portion of the ultrasonic monitor module which faces the subject's wrist and keeps the biocompatible oil-based transmission medium in place.

5. The ultrasonic monitor of claim 1, wherein:
    the ultrasonic monitor module includes a protective layer which encompasses the ultrasonic transmitter and the ultrasonic receiver; and
    the surface is an exposed area of the protective layer, and said biocompatible oil-based transmission medium is positioned over and in contact with the exposed area of the protective layer.

6. The ultrasonic monitor of claim 1, wherein:
    the biocompatible oil-based transmission medium is provided in an over-molding which is over-molded onto a housing of the ultrasonic monitor module, the housing encapsulates a printed circuit board on which the ultrasonic transmitter and the ultrasonic receiver are provided.

7. The ultrasonic monitor of claim 1, wherein:
    the biocompatible oil-based transmission medium extends entirely across the surface.

8. The ultrasonic monitor of claim 1, wherein:
    the biocompatible oil-based transmission medium has a melting point between 50 degrees and 75 degrees Celsius, and a consistency which is defined according to a viscosity between 100,000 to 2,000,000 centipoises, and a cone-penetration of 60 to 120, using a cone penetration measurement according to ASTM D-937.

9. The ultrasonic monitor of claim 1, wherein:
    the biocompatible oil-based transmission medium is provided as a disposable component, and extends entirely across said ultrasonic monitor module.

10. The ultrasonic monitor of claim 1, wherein:
    the natural wax is one or more of beeswax, carnauba wax and candelilla wax.

11. The ultrasonic monitor of claim 1, wherein:
    the oil provides fragrance.

12. The ultrasonic monitor of claim 1, wherein:
    the oil acts a moisturizer for the skin.

13. The ultrasonic monitor of claim 1, wherein:
    the oil has a healing effect on skin tissue.

14. The ultrasonic monitor of claim 13, wherein:
    the oil is an essential oil.

15. The ultrasonic monitor of claim 1, wherein the oil is a natural oil with a butter consistency at room temperature.

16. The ultrasonic monitor of claim 15, wherein
    the natural oil is one or more of coconut butter, cocoa butter, jojoba butter, shea butter, and lanolin.

17. The ultrasonic monitor of claim 1, wherein the oil is a plant based oil.

18. The ultrasonic monitor of claim 1, wherein the oil is petrolatum.

19. The ultrasonic monitor of claim 1, wherein the oil is mineral oil.

20. A method for monitoring a heart rate, comprising:
    applying a biocompatible oil-based transmission medium so that it is between, and in contact with, a surface of an ultrasonic monitor module and a subject's skin, the ultrasonic monitor module is attached to a wrist strap which is adapted to be worn around a wrist of the subject, and the biocompatible oil-based transmission medium consists of natural wax and oil;
    transmitting an ultrasonic signal from the ultrasonic monitor module through the biocompatible oil-based transmission medium to the subject's skin;

receiving a reflected ultrasonic signal by the ultrasonic monitor module through the biocompatible oil-based transmission medium from the subject's skin; and processing the received ultrasonic signal.

21. The method of claim 20, wherein said oil is a natural oil which is one or more of almond oil, aloe vera oil, apricot kernel oil, avocado oil, calendula oil, evening primrose oil, grape seed oil, hazelnut oil, jojoba oil, macadamia oil, olive oil, pumpkin seed oil, rose hip oil, safflower oil, sesame oil, sunflower oil, walnut oil, wheat germ oil, canola oil, coconut oil, tea tree oil, and vitamin E oil.

22. The method of claim 20, wherein:
the biocompatible oil-based transmission medium is applied to the ultrasonic monitor module by heating the biocompatible oil-based transmission medium to a molten state and over-molding the biocompatible oil-based transmission medium onto a housing of the ultrasonic monitor module, the housing encapsulates a printed circuit board on which an ultrasonic transmitter and an ultrasonic receiver are provided.

23. The method of claim 20, wherein:
the surface of the ultrasonic monitor module is an exposed surface of a protective layer, the protective layer encapsulates an ultrasonic transmitter and an ultrasonic receiver provided on a printed circuit board within the ultrasonic monitor module; and
the biocompatible oil-based transmission medium is applied to the exposed surface of the protective layer.

24. The method of claim 20, wherein the biocompatible oil-based transmission medium is provided in, and extends from, an applicator casing, and the applying the biocompatible oil-based transmission medium comprises:
using the applicator casing to apply the biocompatible oil-based transmission medium to at least one of the subject's skin and the surface of the ultrasonic monitor module.

25. The method of claim 20, wherein the biocompatible oil-based transmission medium is provided in a pad having a pressure-sensitive adhesive, the pad is between protective covers, and the applying the biocompatible oil-based transmission medium comprises:
removing the protective covers and adhering the pad to the subject's skin and the surface of the ultrasonic monitor module.

26. An ultrasonic monitor comprising:
an ultrasonic monitor module attached to a wrist strap and adapted to be worn around a wrist of a subject, the ultrasonic monitor module has a surface which faces the wrist, and the ultrasonic monitor module includes an ultrasonic transmitter and an ultrasonic receiver sealed within the ultrasonic monitor module;

a gel pad in contact with said surface of said ultrasonic monitor module; and a biocompatible oil-based transmission medium in contact with said gel pad and skin of the subject's wrist, said gel pad and said biocompatible oil-based transmission medium are arranged between said ultrasonic monitor module and the subject's skin in a path of ultrasonic signals, and the biocompatible oil-based transmission medium consists of natural wax and oil.

27. The ultrasonic monitor of claim 26, wherein said oil is a natural oil which is one more of almond oil, aloe vera oil, apricot kernel oil, avocado oil, calendula oil, evening primrose oil, grape seed oil, hazelnut oil, jojoba oil, macadamia oil, olive oil, pumpkin seed oil, rose hip oil, safflower oil, sesame oil, sunflower oil, walnut oil, wheat germ oil, canola oil, coconut oil, tea tree oil, and vitamin E oil.

28. The ultrasonic monitor of claim 26, wherein said gel pad includes a membrane layer.

29. A method for monitoring a heart rate, comprising:
applying a balm to at least one of an ultrasonic monitor module and a subject's wrist skin, an ultrasonic transmitter and an ultrasonic receiver are provided and sealed within the ultrasonic monitor module, a wrist strap is attached to the ultrasonic monitor module, the balm consists of natural wax and natural oil, the natural wax is one or more of beeswax, carnauba wax and candelilla wax; and
fastening the ultrasonic monitor module to the subject's wrist using the wrist strap, so that the balm is positioned between, and in contact with, the ultrasonic monitor module and the subject's wrist skin, and so that ultrasonic signals pass through the balm.

30. The method of claim 29, wherein the balm is provided in an applicator which includes a casing, and the balm extends from the casing to be directly applied to a surface, and the applying the balm comprises:
using the applicator to apply the balm to the at least one of the subject's wrist skin and the ultrasonic monitor module.

31. The method of claim 29, wherein: the balm is provided in a recessed area of the ultrasonic monitor module which faces the subject's wrist skin and keeps the balm in place.

32. The method of claim 29, wherein the balm is provided in a pad having a pressure-sensitive adhesive, the pad is between protective covers, and the applying the balm comprises:
removing the protective covers and adhering the pad to the subject's wrist skin and the ultrasonic monitor module.

* * * * *